United States Patent [19]

Abraham et al.

[11] Patent Number: 4,806,685
[45] Date of Patent: Feb. 21, 1989

[54] 1,1,2-TRIPHENYLPROPANE AND -PROPENE DERIVATIVES

[75] Inventors: Gizella Abraham, Szeged; Tibor Horvath, Budapest; Lajos Toldy, Budapest; Janos Borvendeg, Budapest; Endre Csanyi, Budapest; Eva Kiss, Budapest; Ilona S. nee Hermann, Budapest; Kalman Tory, Budapest, all of Hungary

[73] Assignee: Gyogyszerkutato Inteezet/Pharmaceutical Research Institute, Budapest, Hungary

[21] Appl. No.: 825,777

[22] Filed: Jan. 31, 1986

Related U.S. Application Data

[63] Continuation of Ser. No. 763,078, Aug. 5, 1985, abandoned, which is a continuation of Ser. No. 490,734, May 4, 1983, abandoned, which is a continuation of Ser. No. 185,679, Sep. 10, 1980, abandoned.

[51] Int. Cl.$^4$ .............................................. C07C 93/06
[52] U.S. Cl. .................................. 564/324; 544/397; 549/555; 260/349
[58] Field of Search ................... 564/324; 260/501.18; 514/648

[56] References Cited

U.S. PATENT DOCUMENTS 3,198,833  8/1965  Bergi et al. ........................ 564/381
3,712,929  1/1973  Middleton ...................... 564/324 X
4,536,516  8/1985  Harper et al. .................. 564/324 X

FOREIGN PATENT DOCUMENTS 1099093  1/1968  United Kingdom ............... 564/324

Primary Examiner—Robert V. Hines
Attorney, Agent, or Firm—Young & Thompson

[57] ABSTRACT

A novel 1,1,2-triphenylpropene derivative, namely:

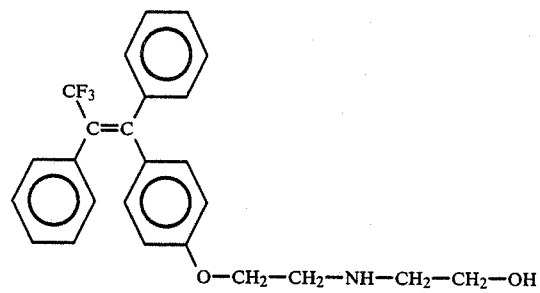

acts on the endocrine system of rats. It exerts oestrogenic or antioestrogenic effects of varying strength in rats, and furthermore inhibits the growth of the mammary tumor induced by 7,12-dimethyl-benz(a)anthracene in rats.

1 Claim, No Drawings

1,1,2-TRIPHENYLPROPANE AND -PROPENE DERIVATIVES

This is a continuation of application Ser. No. 763,078, filed Aug. 5, 1985, now abandoned, which is a continuation of application Ser. No. 490,734, filed May 4, 1983, now abandoned, which is a continuation of Ser. No. 185,679 filed Sept. 10, 1980, now abandoned.

The invention relates to new 1,1,2-triphenylpropane and -propene derivatives.

It is known that some triphenylalkene derivatives possess oestrogenic properties (J. Grundy: Chem. Rev. 57, 281 (1957); P. R. Carter et al.: J. Chem. Soc. 1948, 150; N. P. Buu-Hoi et al.: Chim. Ther. 1969, 327; W. J. Middleton et al.: J. Med. Chem. 14, 1193 (1971); U.S. Pat. No. 3,712,929). Analogous derivatives with a basic substituent on the phenyl ring possess primarily antioestrogenic effects (D. J. Collins et al.: J. Med. Chem. 14, 952 (1971)). The two most important representatives of these compounds are 1-[4-(2-diethylaminoethoxy)-phenyl]-1,2-diphenyl-2-chloroethylene (Clomifen) and (Z)-1-[4-(2-dimethylaminoethoxy)-phenyl]-1,2-diphenyl-1-butene (Tamoxifen)—see F. P. Palopoli et al.: J. Med. Chem. 10, 84 (1966); G. R. Bedford et al.: Nature 212, 733 (1966). Although both compounds show antioestrogenic (oestrogen-antagonizing and slight oestrogen-agonizing) activities, the former compound is applied primarily to induce ovulation (M. Murray et al.: J. Obstet. Gynaec. Br. Commonw. 78, 1108 (1971)) and in the treatment of oligospermy (J. F. Potts: J. Am. Med. Ass. 231, 907 (1975)), whereas the main field of use of Tamoxifen is the treatment of mammary tumors (M. P. Cole et al.: Brit. J. Cancer 1971, 270). Both compounds have, however, the disadvantage that upon prolonged treatment undesired side effects, such as eye damages (H. J. Silverman: Am. J. Optom. 49, 335 (1972); L. M. Roch et al.: Arch. Ophtalm. 77, 14 (1967); M. J. Kaiser-Kupfer et al.: Cancer Treatment Rep. 62, 315 (1978)) liver damages (Martindale: The Extra Pharmacopoeia XXVII. 1392 (1977); The Pharmaceutical Press, London), and thrombosis (K. Nevasaari et al.: Lancet, 946 (1978)) appear.

The new compounds according to the invention exert various effects on the endocrinous systems, of rats and greatly inhibit the growth of mammary tumors induced experimentally by 7,12-dimethyl-benz(a)anthracene (DMBA) in rats.

The new 1,1,2-triphenylpropane and -propene derivatives according to the invention correspond to the general formula (I),

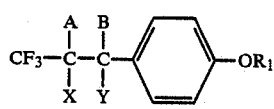

wherein
A and B each stand for hydrogen or they form together a valence bond,
X and Y are identical or different and stand for phenyl group or a phenyl group having a halogen, hydroxy, methoxy-methoxy, $C_{1-6}$ alkoxy or benzyloxy substituent in the para position,
$R_1$ is a $C_{1-6}$ alkyl, epoxyalkyl, azidoalkyl, methoxymethyl or benzyl group or a group of the general formula (II),

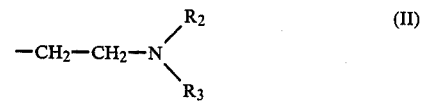

wherein $R_2$ and $R_3$ each represent hydrogen or a $C_{1-6}$ alkyl, hydroxyalkyl or haloalkyl group, or $R_2$ and $R_3$ form together with the adjacent nitrogen atom an up to 8-membered heterocyclic group, an up to 6-membered heterocyclic group optionally containing further hetero atom(s), which heterocyclic groups optionally have a lower alkyl or hydroxyalkyl substituent, a guanidino group, an aminoguanidino group or a nitroguanidino group, with the proviso that if A and B form together a valence bond and X and Y each stand for phenyl or X is phenyl and Y is p-methoxyphenyl, $R_1$ may not stand for a dimethylaminoethyl, diethylaminoethyl, pyrrolidinoethyl, piperidinoethyl or morpholinoethyl group in the (Z) isomers, with the further proviso that
(a) if A and B form together a valence bond and X and Y each stand for phenyl, then $R_1$ may not stand for methyl or ethyl,
(b) if A and B form together a valence bond and X and Y each stand for phenyl, then in the case of the (Z) isomers $R_1$ may not stand for dimethylaminoethyl, diethylaminoethyl, morpholinoethyl or piperidinoethyl,
(c) if A and B form together a valence bond, X stands for phenyl and Y stands for paramethoxyphenyl, then $R_1$ may not stand for methyl or pyrrolidinoethyl,
(d) if A and B form together a valence bond, X stands for paramethoxyphenyl, parafluorophenyl or paraethoxyphenyl, and Y stands for phenyl, then $R_1$ may not stand for methyl,
(e) if A and B form together a valence bond, X is phenyl and Y is parahydroxyphenyl, then $R_1$ may not stand for methyl, and
(f) if A and B form together a valence bond, and X and Y each stand for paramethoxyphenyl, then $R_1$ may not stand for methyl.

Stereoisomers and isomeric mixtures of the above compounds, furthermore acid addition salts of the basic compounds having the general formula (I) are also embraced by the scope of the invention.

The term "alkyl group", used either alone or in combinations (such as alkoxy, azidoalkyl, epoxyalkyl, hydroxyalkyl or haloalkyl) refers to a straight-chained or branched saturated aliphatic hydrocarbyl group of 1 to 6, preferably 1 to 4 carbon atoms (such as methyl, ethyl, n-propyl, isopropyl, n-butyl, sec.-butyl, etc., preferably methyl or ethyl group). The term "halogen" embraces all the four halogens, i.e. fluorine, chlorine, bromine and iodine. If $R_2$ and $R_3$ form together with the adjacent nitrogen atom an optionally alkyl- or hydroxyalkyl-substituted heterocyclic group, this group may be preferably a pyrrolidino, piperidino, heptamethyleneimino, morpholino, piperazino or N-methylpiperazino group.

In a preferred subgroup of the compounds having the general formula (I) A and B form together a valence bond.

Those compounds of the general formula (I) are also preferred, in which A and B each stand for hydrogen or they form together a valence bond, X and Y are identical or different and stand for a phenyl or p-hydroxyphenyl group, and $R_1$ represents a $C_{1-4}$ ethoxyalkyl group, a $C_{1-4}$ azidoalkyl group or a group of the general formula (II), wherein $R_2$ and $R_3$ each stand for hydrogen, a $C_{1-4}$ alkyl group or a $C_{1-4}$ hydroxyalkyl group or they form, together with the adjacent nitrogen atom, a piperazino, pyrrolidino, piperidino or morpholino group having optionally a $C_{1-4}$ alkyl substituent.

Particularly preferred representatives of the compounds of the general formula (I) are the following derivatives: threo-1-[4-(2,3-epoxypropoxy)-phenyl]-1,2-diphenyl-3,3,3-trifluoro-propane, (E)-1,2-diphenyl-3,3,3-trifluoro-1-[4-(2-[4-methylpiperazino]-ethoxy)-phenyl]-propene, 1-[4-(2-dimethylaminoethoxy)-phenyl]-2-phenyl-3,3,3-trifluoro-1-(4-hydroxyphenyl)-propene, (E)1,2-diphenyl-3,3,3-trifluoro-1-[4-(2-[2-hydroxyethylamino]-ethoxy)-phenyl]-propene, (E)-1-[4-(2-azidoethoxy)-phenyl]-1,2-diphenyl-3,3,3-trifluoro-propene, 1-[4-(2-dimethylamino-ethoxy)-phenyl]-3,3,3-trifluoro-1,2-bis-(4-hydroxyphenyl)-propene and pharmaceutically acceptable acid addition salts thereof.

The basic compounds of the general formula (I) form acid addition salts with mineral or organic acids, such as hydrochloric, hydrobromic, sulfuric, phosphoric, maleic, fumaric, lactic, methanesulfonic, p-toluenesulfonic, citric, etc. acids.

The compounds of the general formula (I) can be presented in the form of various stereoisomers, such as (Z) and (E) isomers, threo and erythro isomers. All of the stereoisomers and mixtures thereof, furthermore their preparation as well as the pharmaceutical compositions which contain such isomers or isomeric mixtures are embraced by the scope of the invention.

These compounds are prepared according to the invention as follows:

(a) to prepare a compound of the general formula (I) in which A and B are as defined above, X and Y are identical or different and represent a phenyl group, a p-halophenyl group or a p-($C_{1-6}$ alkoxy)-phenyl group, $R_1$ stands for azidoethyl group or a group of the general formula (II), wherein $R_2$ and $R_3$ are as defined above, a phenoxyalkylhalide or sulfonate of the general formula (III),

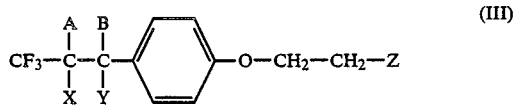

(III)

wherein A and B are as defined above, Y and X are as defined in point (a) and Z stands for halogen or a sulfonyloxy group, is reacted with an amine of the general formula $R_2R_3NH$, wherein $R_2$ and $R_3$ are as defined above, or with an alkali metal azide, and, if desired, the resulting azido derivative is reduced, and, if desired, a resulting amino derivative is converted into the respective guanidino, aminoguanidino or nitroguanidino derivative; or (b) to prepare a compound of the general formula (I) in which A and B form together a valence bond, X and Y are identical or different and represent an unsubstituted phenyl group or a phenyl group which has a chloro, bromo, methoxymethoxy, $O_{1-6}$ alkoxy or benzyloxy substituent in the para position, and $R_1$ stands for a group of the general formula (II), wherein $R_2$ and $R_3$ each represent hydrogen or a $C_{1-6}$ alkyl group, or $R_2$ and $R_3$ form together with the adjacent nitrogen atom an up to 8-membered heterocyclic group or an up to 6-membered heterocyclic group optionally containing further hetero atom(s), which heterocyclic groups optionally have a lower alkyl or hydroxyalkyl substituent, a compound of the general formula (IV),

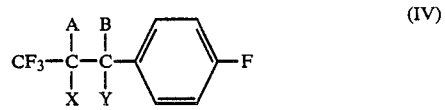

(IV)

wherein A and B stand for hydrogen and X and Y are as defined in point (b) above, is dehydrogenated and then reacted with an alcohol derivative of the general formula $R_1OM$, wherein $R_1$ is as defined in point (b) and M stands for an alkali metal atom; or (c) to prepare a compound of the general formula (I) in which A and B are as defined above, X and Y are identical or different and represent an unsubstituted phenyl group or a phenyl group having a halogen or $C_{1-6}$ alkoxy substituent in the para position and $R_1$ stands for a $C_{1-6}$ alkyl, epoxyalkyl, methoxymethyl or benzyl group or represents a group of the general formula (II), wherein $R_2$ and $R_3$ each stand for a $C_{1-6}$ alkyl group or they form together with the adjacent nitrogen atom an up to 8-membered heterocyclic group or an up to 6-membered heterocyclic group optionally containing further hetero atom(s), which heterocyclic groups optionally have a lower alkyl substituent, a compound of the general formula (V),

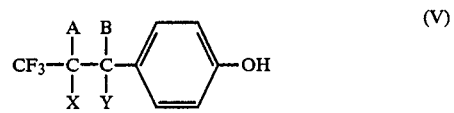

(V)

wherein A and B are as defined above and X and Y are as defined in point (c), is reacted with an $R_1$-halide or an $R_1$-sulfonate, wherein $R_1$ is as defined in point (c) above, in the presence of an acid binding agent; or (d) to prepare a compound of the general formula (I) in which A and B form together a valence bond, X and/or Y stands for a p-hydroxyphenyl group and $R_1$ is a group of the general formula (II), wherein $R_2$ and $R_3$ each represent hydrogen or a $C_{1-6}$ alkyl group or they form together with the adjacent nitrogen atom an up to 8-membered heterocyclic group or an up to 6-membered heterocyclic group optionally containing further hetero atom(s), which heterocyclic groups optionally have a lower alkyl substituent, a compound of the general formula (IV), wherein A and B are as defined in point (d) and X and/or Y is a p-(methoxymethoxy)-phenyl group or a benzyloxyphenyl group, is reacted with an alcohol derivative of the general formula $R_1OM$, wherein $R_1$ is as defined in point (d) and M is an alkali metal atom, and then the methoxymethoxy group or the benzyloxy group is subjected to an ether splitting reaction; or (e) to prepare a compound of the general formula (I) in which A and B form together a valence bond, X and Y are identical or different and stand for an unsubstituted phenyl group or a phenyl group which has a halo, methoxymethoxy, $C_{1-6}$ alkoxy or benzyloxy substituent in the para position and $R_1$ represents a $C_{1-6}$ alkyl, epoxyalkyl, azidoethyl, methoxymethyl or benzyl group, a compound of the general formula (I), wherein A and B each stand for hydrogen and X, Y and $R_1$ are as defined in point (e), is dehydrogenated; or (f) to prepare a compound of the general formula (I) in which $R_1$ represents a group of the general formula (II) and in this latter formula $R_2$ and/or $R_3$ stands for a $C_{1-6}$ haloalkyl group, a compound of the general formula (I), wherein $R_1$ is a group of the general formula (II) and in this latter formula $R_2$ and/or $R_3$ represent a $C_{1-6}$ hydroxyalkyl group, is halogenated; and, if desired, the individual stereoisomers are separated from a resulting isomeric mixture, and, if desired, a basic compound of the general formula (I) is converted into its acid addition salt or liberated from its acid addition salt.

Proces variant (a) of the invention is performed preferably so that the starting substance of the general formula (III) is heated with an amine of the general formula $R_2R_3NH$ in an inert solvent or diluent (such as alcohol, aqueous alcohol, acetone, etc.) in the presence of an acid binding agent (such as potassium carbonate or an excess of the amine reactant), or is reacted with an alkali metal azide in dimethylformamide or preferably in aqueous 2-methoxyethanol. If desired, a resulting azido derivative can be reduced in a manner known per se e.g. with an alkali metal hydride or with hydrogen in the presence of palladium-on-carbon catalyst.

In the starting substances of the general formula (III) Z is preferably a halogen atom (fluorine, chlorine, bromine or iodine), an alkylsulfonyloxy group (e.g. methylsulfonyloxy group) or an arylsulfonyloxy group (e.g. an optionally substituted phenylsulfonyloxy group, such as phenylsulfonyloxy, p-toluenesulfonyloxy or p-bromophenylsulfonyloxy group).

Process variant (b) of the invention is performed preferably so that a compound of the general formula (IV), wherein A and B stand for hydrogen, is reacted with 1 to 3 molar equivalents of 2,3-dichloro-5,6-dicyano-1,4-benzoquinone in an inert solvent (e.g. benzene or dioxane) at the boiling point of the reaction mixture, and the resulting compound is reacted with an alcohol derivative of the general formula $R_1OM$ in a bipolar aprotic solvent (e.g. dimethyl acetamide, hexamethylphosphoric triamide, etc.) or preferably in an excess of the alcohol of the general formula $R_1OH$. This latter reaction is performed preferably at 100° to 160° C.

According to process variant (c) of the invention a phenol derivative of the general formula (V) is reacted with an $R_1$-halide or an $R_1$-sulfonate in a solvent or diluent, such as benzene, alcohol, etc., in the presence of an acid binding agent, such as an alkali metal hydroxide or an alkali metal carbonate. According to a preferred method the process is performed with an alkali metal salt of the starting phenol derivative, which also serves as acid binding agent.

Process variant (d) of the invention is performed preferably as described above for process variant (b). The resulting methoxymethoxy or benzyloxy derivative is treated then with an acid or reduced to effect the splitting of the ether group.

In process variant (a) of the invention a compound of the general formula (I), wherein A and B each stand for hydrogen, is dehydrogenated. Dehydrogenation is performed preferably by reacting the starting substance with 2,3-dichloro-5,6-dicyano-1,4-benzoquinone in an inert solvent (e.g. benzene or dioxane) at the boiling point of the reaction mixture (see Org. Synth. Coll. Vol. 5, 428–431).

According to process variant (f) of the invention a compound of the general formula (I), wherein $R_1$ is a group of the general formula (II) and in this latter formula $R_2$ and/or $R_3$ stands of hydroxyalkyl, is reacted with a halogenating agent to obtain the respective derivative wherein $R_2$ and/or $R_3$ is a haloalkyl group. Halogenation is performed in a manner known per se, utilizing conventional halogenating agents, such as thionyl chloride, etc.

The individual stereoisomers can be separated from their mixtures by methods known per se, such as fractional crystallization.

The basic compounds of the general formula (I) can be converted into their acid addition salts by reacting them with the appropriate acid in an inert solvent. Of the acid addition salts those formed with pharmaceutically acceptable acids are preferred. The bases can be liberated from the respective acid addition salts by treatment with a strong base.

The starting substances of the general formulae (III), (IV) and (V) are, with the exception of (Z)-1,2-diphenyl-3,3,3-trifluoro-1-(4-fluorophenyl)-propene, (Z)-1,2-diphenyl-3,3,3-trifluoro-1-(4-hydroxyphenyl)-propene and (E)-2-phenyl-3,3,3-trifluoro-1-(4-hydroxyphenyl)-1-(4-methoxyphenyl)-propene, new compounds. The preparation of the new starting substances is described in detail in the examples.

The endocrinological and tumor-inhibitory effects of the new compounds according to the invention are demonstrated by the following tests. The compounds tested are listed below:

1 = threo-1-[4-(2,3-epoxypropoxy)-phenyl]-1,2-diphenyl-3,3,3-trifluoro-propane,
2 = (E)1-[4-(2,3-epoxypropoxy)-phenyl]-1,2-diphenyl-3,3,3-trifluoro-propene,
3 = (E)-1,2-diphenyl-3,3,3-trifluoro-1-[4-(2-[bis-(2-hydroxyethyl)-amino]-ethoxy)-phenyl)]-propene,
4 = (E)-1,2-diphenyl-3,3,3-trifluoro-1-[4-(2-[4-methylpiperazino]-ethoxy)-phenyl]-propene,
5 = 1-[4-(2-dimethylaminoethoxy)-phenyl]-2-phenyl-3,3,3-trifluoro-1-(4-methoxyphenyl)-propene,
6 = 1-[4-(2-dimethylaminoethoxy)-phenyl]-2-phenyl-3,3,3-trifluoro-1-(4-hydroxyphenyl)-propene,
7 = (E)-1,2-diphenyl-3,3,3-trifluoro-1-[4-(2-[2-hydroxyethylamino]-ethoxy)-phenyl]-propene,
8 = 1-[4-(2-dimethylaminoethoxy)-phenyl]-1-phenyl-3,3,3-trifluoro-2-(4-hydroxyphenyl)-propene,
9 = (E)-1,2-diphenyl-3,3,3-trifluoro-2-[4-(2-pyrrolidinoethoxy)-phenyl]-propene,
10 = (E)-1,2-diphenyl-3,3,3-trifluoro-1-[4-(2-morpholinoethoxy)-phenyl]-propene,
11 = (E)-1-[4-(2-diethylaminoethoxy)-phenyl]-1,2-diphenyl-3,3,3-trifluoro-propene,
12 = (E)-1-[4-(2-azidoethoxy)-phenyl]-1,2-diphenyl-3,3,3-trifluoro-propene,
13 = (E)-1,2-diphenyl-3,3,3-trifluoro-1-[4-(2-[bis-(2-chlorethyl)-amino]-ethoxy)-phenyl]-propene,
14 = 1-[4-(2-dimethylaminoethoxy)-phenyl]-3,3,3-trifluor-1,2-bis-(4-hydroxyphenyl)-propene hydrochloride,
15 = 1-phenyl-2-(4-methoxyphenyl)-1-[4-(2-dimethylaminoethoxy)phenyl]-3,3,3-trifluoro-propene,
16 = (E)-1,2-diphenyl-3,3,3-trifluoro-1-[4-(2-[nitroguanidino]ethoxy)-phenyl]-propene.

The antioestrogenic effect was determined by the method of M. J. K. Harper et al. (J. Reprod. Fert. 13, 101 (1967)). 24 days old infantile female rats were treated with daily dosages of 5 μg/kg of oestradiol for 3 days. The test compound was also administered once a day orally for 3 days. On the 4th day the animals were sacrificed, and their uterus was removed and weighed.

maximum increase in uterine weight attainable at higher dose ranges (10 mg/kg) with Compound No. 1 is higher than that attainable by the antioestrogenic agents.

TABLE 2

| Compound tested | Determination of the uterotropic (oestrogenic) effect on infantile female rats Dosage mg/kg/day p.o. | | | | | | | | |
|---|---|---|---|---|---|---|---|---|---|
| | 0 | 0.01 | 0.03 | 0.1 | 0.3 | 1.0 | 3.0 | 10.0 | 20.0 |
| Ethynyl- | 59.3 ± 5.2 | 142.6 ± 5.2 | 197.0 ± 11.75 | 184.6 ± 7.6 | 198.4 ± 14.9 | 166.8 ± 9.34 | 192.2 ± 4.3 | 212.2 ± 11.8 | |
| Tamoxifen | 41.5 ± 1.36 | 75.0 ± 3.76 | 79.0 ± 2.67 | 102.3 ± 4.35 | 96.2 ± 4.04 | 108.3 ± 6.97 | 113.0 ± 3.88 | 110.1 ± 4.5 | 101.0 |
| Clomifen | 41.5 ± 1.36 | | | 107.3 ± 6.48 | | 103.4 ± 6.38 | | 94.4 ± 2.35 | |
| 1 | 41.5 ± 1.36 | 49.2 ± 3.48 | 52.2 ± 2.67 | 65.8 ± 5.7 | 72.0 ± 4.6 | 118.2 ± 9.9 | 130.6 ± 11.2 | 142.0 ± 10.47 | 138.0 |
| 2 | 59.3 ± 5.2 | 84.5 ± 4.33 | 87.5 ± 8.7 | 90.8 ± 3.4 | 95.0 ± 3.14 | 101.2 ± 4.3 | 107.0 ± 2.19 | 128.4 ± 5.83 | |
| 3 | 41.5 | 66 | 79 | 99 | 102 | 104 | 106 | 114 | |
| 4 | 59.3 ± 5.2 | 76.6 ± 4.4 | 86.6 ± 6.6 | 89.8 ± 10.6 | 91.0 ± 2.16 | 97.2 ± 4.43 | 100.8 ± 0.7 | 110.8 ± 6.18 | |
| 7 | 59.3 ± 5.2 | 72.0 ± 2.7 | 73.7 ± 4.5 | 89.6 ± 5.0 | 96.0 ± 5.8 | 101.0 ± 1.9 | 99.4 ± 4.07 | 112.2 ± 8.0 | |
| 8 | 59.3 ± 5.2 | 83.9 ± 4.7 | 79.5 ± 5.4 | 78.0 ± 3.4 | 92.2 ± 1.6 | 95.8 ± 3.67 | 102.8 ± 3.2 | 106.0 ± 3.4 | |
| 14 | 38.0 ± 2.9 | | | 59.0 ± 1.7 | 74.0 ± 4.3 | 77.0 ± 6.1 | 79.0 ± 2.3 | 78.0 ± 1.2 | |

Remarks:
The tests were performed on groups of 5 to 10 animals.
The weight of the uterus is given as mg/100 kg body weight.

The date characteristic of the antioestrogenic activity (inhibition of the uterotropic effect of oestradiol) of some compounds according to the invention are listed in Table 1.

The antioestrogenic activity of some of the compounds listed in Table 1 reaches the activity of Clomifen or Tamoxifen, applied as reference substances. Compound No. 1 produces, however, only a slight inhibition when applied in an oral dosage of 1 mg/kg. The degree of inhibition still remains low (39%) when the dosage is increased to 10 mg/kg.

TABLE 1

| Compound tested | Determination of the antioestrogenic effect on infantile female rats Dosage mg/kg/day | | | | |
|---|---|---|---|---|---|
| | 0.1 | 0.3 | 1.0 | 3.0 | 10.0 |
| Clomifen | −37.1 | | −67.7 | | −73.3 |
| Tamoxifen | −45.6 ± 6.85 | −55.2 ± 2.5 | −60.9 ± 4.04 | −70.9 ± 4.52 | −68.6 ± 4.83 |
| 1 | | | −3.0 | | |
| 2 | −29 | −24 | −38 | −78 | −66 |
| 3 | −14 | −53 | −59 | −67 | −73 |
| 4 | | −65.2 ± 3.93 | −71.9 ± 1.81 | −71.8 ± 5.0 | −72.2 ± 5.5 |
| 5 | −52.8 ± 4.2 | −52.2 ± 6.12 | −60.8 ± 2.13 | −68.2 ± 3.32 | −63.0 ± 3.68 |
| 6 | −37.0 ± 5.3 | −35.7 ± 3.85 | −48.4 ± 8.61 | −51.6 ± 3.49 | −61.0 ± 3.9 |
| 7 | −26.5 ± 2.98 | −49.2 ± 2.1 | −68.5 ± 5.14 | −60.4 ± 2.5 | −51.0 ± 8.1 |
| 8 | −26 | −29 | −54 | −61 | |
| 14 | −31 | −32 | −43 | −50 | −61 |

Remarks:
The antioestrogenic (uterus weight lowering) effects of the compounds are given in percents.
The tests were performed on groups of 5 to 10 animals.

The oestrogenic (uterotropic) effect was determined according to the method of R. J. Dorfman (Endocrinology 55, 65 (1954)). 24 days old female rats were treated with single daily oral dosages of the test compounds. On the 4th day the animals were sacrificed, and their uterus was removed and weighed. The data characteristic of the oestrogenic (uterotropic) effects of some of the compounds according to the invention are listed in Table 2. Ethynyloestradiol, a highly effective oestrogenic substance, and Clomifen and Tamoxifen, two known antioestrogenic agents, were also tested and their activity data are also presented.

The compounds listed in Table 2 possess generally weak oestrogenic properties, or, in the dosage range of 0.1 to 1.0 mg/kg, their activity is somewhat lower than that of Tamoxifen. The dosage-activity curve of Compound No. 1 is, however, somewhat steeper than those of the other compounds. Thus, in the lower dosage range (0.01 to 3.0 mg/kg) applied, the oestrogenic effect of Compound No. 1 is even weaker than the weak agonistic effects of the antioestrogenic agents, whereas the The stimulating effect exerted on the secretion of luteinizing hormone (LH) was determined as follows: 24 days old infantile female rats were treated subcutaneously with the compounds to be tested on two consecutive days. Two hours after the second treatment the animals were bled and the luteinizing hormone (LH) level of the plasma was determined by radioimmune assay. When administered in subcutaneous dosages of 1 mg/kg, the compounds tested provoke a considerable increase in the LH level of the plasma. The results are summarized in Table 3.

TABLE 3

| | LH-level increasing effect on infantile female rats |
|---|---|
| Compound tested | Percentage change of the LH level in relation to the controls |
| Tamoxifen | 117 |
| 1 | 96 |
| 3 | 134 |
| 4 | 106 |
| 7 | 39 |
| 9 | 53 |

Remarks:
The tests were performed on groups of 4 or 5 animals.
Dosage: 2 × 1 mg/kg s.c.

The effects of the new compounds exerted on hormone-dependent tumours were tested by the method of P. Griswold et al. (Cancer Research 26, 2169 (1966)) on mammary cancer induced by 7,12-dimethyl-benz(a)anthracene (DMBA). The treatment was started when the weight of the tumor reached about 500 mg, and the animals were treated for 3 months with oral dosages of 20 mg/kg of the active agent, administered three times a week. The size of the tumors was measured as described by the above authors as well as according to the method of V. C. Jordan et al. (Europ. J. Cancer 12, 419 (1976)), with a caliper gauge. The volume of the tumor was determined by the method of Griswold. The animals were kept under observation for 2 additional months after the termination of the treatment period, and the tumors were measured in this latter period as well.

A relative effectivity index was introduced to characterize the activities of the compounds tested. To calculate the relative effectivity index the number of animals showing a permanent or transitory cure or remission of various durations was determined and scored according to the following table:

permanently cured: 10 points
temporarily cured: 8 points
durable remission: 6 points
short remission or unchanged state: 4 points.

The changes in average tumor number appearing during the treatment period were evaluated according to the following scale:

no increase in tumor count in any of the animals: 8 points
the average number of tumors increases twofold: 6 points
higher increase in the average number of tumors: 0 points.

The score numbers determined for the individual animals by the above two scales were added, and the result was expressed in percents related to the score number which corresponds to the maximum activity (permanent cure). This percentage value is the relative effectivity index.

The results of the test are listed in Table 4, where the figures in brackets have the following meanings: (1) permanently cured; (2) temporarily cured; (3) durable remission; (4) short remission; (5) unchanged state.

TABLE 4

| Compound tested | Activity | | | | | Relative effectivity index |
|---|---|---|---|---|---|---|
| | (1) | (2) | (3) | (4) | (5) | |
| Untreated controls | — | — | — | — | 25/25 | 0 |
| Tamoxifan | 2/5 | 1/5 | — | 1/5 | 1/5 | 70 |
| 1 | 4/5 | 1/5 | — | — | — | 96 |
| 3 | 1/5 | 1/5 | — | 3/5 | — | 65 |
| 4 | — | — | 3/4 | 1/4 | — | 60 |
| 6 | 2/5 | 1/5 | 1/5 | — | 1/5 | 78 |
| 7 | 2/5 | 1/5 | 1/5 | — | 1/5 | 78 |
| 10 | 4/5 | — | — | — | 1/5 | 90 |
| 11 | 1/5 | — | 3/5 | — | 1/5 | 72 |
| 12 | 2/5 | 2/5 | 1/5 | — | — | 85 |
| 13 | 1/5 | 1/5 | 1/5 | 2/5 | — | 67 |
| 15 | 2/5 | — | 2/5 | — | 1/5 | 70 |
| 16 | — | 1/4 | 3/4 | — | — | 73 |

The invention is elucidated in detail by the aid of the following non-limiting Examples.

EXAMPLE 1

Preparation of erythro- and threo-1,2-diphenyl-3,3,3-trifluoro-1-[4-(2-morpholinoethoxy)-phenyl]-propane A mixture of 1.20 g (2.67 mmoles) of erythro-1-[4-(2-bromoethoxy)-phenyl]-1,2-diphenyl-3,3,3-trifluoro-propane and 4.80 g of morpholine is heated to boiling, then cooled, diluted with 50 ml of ether and washed with water until neutral. The etheral solution is dried, evaporated to dryness, and the residue is crystallized from hexane. 1.02 g (83.6%) of erythro-1,2-diphenyl-3,3,3-trifluoro-1-[4-(2-morpholinoethoxy)-phenyl]-propane are obtained; m.p.: 112°–115° C.

Analysis: calculated for $C_{27}H_{28}F_3NO_2$: C: 71.19%, H: 6.20%, F: 12.51%, N: 3.08%; found: C: 71.07%, H: 6.37%, F: 12.71%, N: 2.97%.

A mixture of 3.60 g (8 mmoles) of threo-1-[4-(2-bromoethoxy)-phenyl]-1,2-diphenyl-3,3,3-trifluoro-propane and 14 g of morpholine is heated to boiling, and thereafter one proceeds as described above. The resulting product is crystallized from hexane to obtain 2.85 g (78.3%) of threo-1,2-diphenyl-3,3,3-trifluoro-1-[4-(2-morpholinoethoxy)-phenyl]-propane; m.p.: 88°–91° C.

Analysis: calculated for $C_{27}H_{28}F_3NO_2$: C: 71.19%, H: 6.20%, F: 12.51%, N: 3.08%; found: C: 71.24%, H: 6.44%, F: 12.45%, N: 3.03%.

The starting substances, erythro and threo-1-[4-(2-bromoethoxy)-phenyl]-1,2-diphenyl-3,3,3-trifluoro-propane, are prepared as follows:

A solution of 456 g (1.17 moles) of benzyl-triphenyl-phosphoniumchloride (G. Wittig: Chem. Ber. 87, 1318 (1954)) in 1500 ml of dry ethanol is added to a solution of 27 g (1.17 g.-atoms) of sodium in 500 ml of dry ethanol at 0°–2° C. The resulting mixture is combined with a solution of 204 g (1.17 moles) of 2,2,2-trifluoroacetophenone in 100 ml of dry ethanol, and the mixture is allowed to stand overnight. The solution is evaporated, the residue is admixed with 800 ml of petroleum ether, filtered, and the filter cake is washed. The filtrate is evaporated, and the residue is distilled in vacuo. 268 g (92.5%) of 1,2-diphenyl-3,3,3-trifluoro-propane are obtained; b.p.: 107°–109° C./0.2 mm Hg, m.p.: 58°–61° C.

Analysis: calculated for $C_{15}H_{11}F_3$: C: 72.57%, H: 4.47%, F: 22.96%; found: C: 72.49%, H: 4.23%, F: 23.20%.

268 g (1.08 moles) of the above product are hydrogenated at 20° C. for 6–8 hours in 4000 ml of acetic acid, in the presence of 20 g of a 10% palladium-on-carbon catalyst. The solution is evaporated and the residue is distilled in vacuo. 252 g (93.3%) of 1,2-diphenyl-3,3,3-trifluoro-propane are obtained; b.p.: 94°–96° C./0.1 mm Hg, $n_D^{20}$=1.5100.

Analysis: calculated for $C_{15}H_{13}F_3$: C: 71.98%, H: 5.26%, F: 22.75% found: C: 72.12%, H: 5.44%, F: 22.50%.

5 g (0.02 moles) of benzoyl peroxide are added to a solution of 250 g (1 mole) of the above product in 2500 ml of carbon tetrachloride, and then a solution of 176 g (1.1 moles) of bromine in 500 ml of carbon tetrachloride is added to the mixture of 50° C. within 30 minutes. The resulting mixture is boiled for 2 hours, then cooled, washed with sodium thiosulfate solution, sodium hydrocarbonate solution and then with water, dried and evaporated. The residue is crystallized from 1260 ml of ethanol to obtain 140 g (42.6%) of erythro-1-bromo-1,2-diphenyl-3,3,3-trifluoro-propane; m.p.: 164°–165° C.

Analysis: calculated for $C_{15}H_{12}BrF_3$: C: 54.73%, H: 3.67%, Br: 24.28%, F: 17.32%; found: C: 54.97%, H: 3.93%, Br: 23.98%, F: 17.36%.

The mother liquor is evaporated to about one-third of its original volume. 130 g (39.5%) of threo-1-bromo-1,2-diphenyl-3,3,3-trifluoro-propane separate; m.p.: 91°–94° C.

Analysis: calculated for $C_{15}H_{12}BrF_3$: C: 54.73%, H: 3.67%, Br: 24.28%, F: 17.32%; found: C: 54.86%, H: 3.82%, Br: 24.01%, F: 17.27%.

The NMR spectra of the compounds confirm the assigned structures.

270 g (0.82 moles) of an erythro-threo isomeric mixture obtained as described above are dissolved in 2500 ml of anisole, 110 g (0.83 moles) of anhydrous aluminium trichloride are added to the stirred solution at 6° C., and the mixture is allowed to stand at room temperature overnight. The reaction mixture is poured onto a mixture of 4 kg of crushed ice and 600 ml of 36% aqueous hydrochloric acid and extracted with 3 liters of chloroform. The organic solution is washed with aqueous sodium hydrocarbonate solution and then with water, dried and evaporated. The dry residue is crystallized from 750 ml of isopropanol, and the resulting crude product (162 g, 55%, m.p.: 121°–126° C.) is crystallized again from 1500 ml of isopropanol. 109 g (37%) of threo-1,2-diphenyl-3,3,3-trifluoro-1-(4-methoxyphenyl)-propane are obtained; m.p.: 129°–131° C.

Analysis: calculated for $C_{22}H_{19}F_3O$: C: 74.14%, H: 5.37%, F: 16.00%; found: C: 74.08%, H: 5.47%, F: 15.75%. Spectral data: $\nu_{CH}$ 3050, 3025, 2995, 2950, 2925, 2900, 2830 $\nu_{C=C}$ 1605, 1580, 1508 $\gamma_{Ar}$ 808, 786, 758, 702 $\delta_{CH(Ar)2}$=4.60 (d), 1H $\delta_{CH(CF3)}$=4.23 (m), 1H $\delta_{OCH3}$=3.60 (s), 1H $\delta_{Ar}$=6.7–7.3 (m), 14H.

The mother liquor obtained in the first crystallization step is evaporated to dryness, the residue is admixed with 300 ml of hexane and filtered. The resulting crude product (96 g, 27%, m.p.: 89°–101° C.) is crystallized again from 960 ml of isopropanol to obtain 41.4 g (14%) of erythro-1,2-diphenyl-3,3,3-trifluoro-1-(4-methoxyphenyl)-propane; m.p.: 108°–111° C.

Analysis: calculated for $C_{22}H_{19}F_3O$: C: 74.14%, H: 5.37%, F: 16.00%; found: C: 74.23%, H: 5.18%, F: 16.17%. Spectral data: $\nu_{CH}$ 3090, 3060, 3025, 3010, 2960, 2940, 2915, 2840 $\nu_{C=C}$ 1658, 1612, 1590, 1513, 1500 $\gamma_{Ar}$ 808, 790, 762, 708, 702 $\delta_{CH(Ar)2}$=4.60 (d), 1H $\delta_{CH(CF3)}$=4.23 (m), 1H $\delta_{OCH3}$=3.60 (s), 3H $\delta_{Ar}$=6.4–7.6 (m), 14H.

100 g (0.28 moles) of threo-1,2-diphenyl-3,3,3-trifluoro-1-(4-methoxyphenyl)-propane are heated with 300 g of pyridine hydrochloride for 3 hours at 200°–220° C. The mixture is cooled, diluted with 700 ml of chloroform, washed with water until neutral, dried and evaporated. The residue is crystallized from a 1:2 mixture of chloroform and hexane to obtain 85.7 g (90%) of threo-1,2-diphenyl-3,3,3-trifluoro-1-(4-hydroxyphenyl)-propane; m.p.: 123°–125° C.

Analysis: calculated for $C_{21}H_{17}F_3O$: C: 73.67%, H: 5.01%, F: 16.65%; found: C: 73.56%, H: 4.92%, F: 16.78%.

40 g (0.11 moles) of erythro-1,2-diphenyl-3,3,3-trifluoro-1-(4-methoxyphenyl)-propane are reacted with 120 g of pyridine hydrochloride as described above. The resulting erythro-1,2-diphenyl-3,3,3-trifluoro-1-(4-hydroxyphenyl)-propane is crystallized from a 1:2 mixture of chloroform and hexane to obtain 32.5 g (84.5%) of the product; m.p.: 114°–117° C.

Analysis: calculated for $C_{21}H_{17}F_3O$: C: 73.67%, H: 5.01%, F: 16.65%; found: C: 73.52%, H: 4.97%, F: 16.71%.

A mixture of 85.6 g (0.25 moles) of threo-1,2-diphenyl-3,3,3-trifluoro-1-(4-hydroxyphenyl)-propane, 400 ml of 1,2-dibromoethane and 18.5 g (0.33 moles) of powdered potassium hydroxide is boiled under stirring. The reaction mixture is diluted with 1.5 liters of dichloromethane, washed with 10% aqueous hydrochloric acid and water, dried, and the solvent and the excess of 1,2-dibromoethane are distilled off in vacuo. The residue is crystallized from benzene to obtain 97.7 g (87%) of threo-1-[4-(2-bromoethoxy)-phenyl]-1,2-diphenyl-3,3,3-trifluoro-propane; m.p.: 144°–151° C.

Analysis: calculated for $C_{23}H_{20}BrF_3O$: C: 61.48%, H: 4.49%, Br: 17.78%, F: 12.68%; found: C: 61.55%, H: 4.57%, Br: 17.63%, F: 12.71%.

30 g (87.6 mmoles) of erythro-1,2-diphenyl-3,3,3-trifluoro-1-(4-hydroxyphenyl)-propane are reacted with 1,2-dibromoethane as described above. The resulting erythro-1-[4-(2-bromoethoxy)-phenyl]-1,2-diphenyl-3,3,3-trifluoropropane is crystallized from benzene to obtain 27.9 g (71%) of the product; m.p.: 130°–133° C.

Analysis: calculated for $C_{23}H_{20}BrF_3O$: C: 61.48%, H: 4.49%, Br: 17.78%, F: 12.68%; found: C: 61.60%, H: 4.63%, Br: 17.60%, F: 12.77%.

EXAMPLE 2

Preparation of threo-1,2-diphenyl-3,3,3-trifluoro-1-[4-(2-/2-hydroxyethylamino/-ethoxy)-phenyl]-propane A mixture of 6.74 g (15 mmoles) of threo-1-[4-(2-bromoethoxy)-phenyl]-1,2-diphenyl-3,3,3-trifluoro-propane, prepared as described in Example 1, 9.15 g (150 mmoles) of 2-aminoethanol and 15 ml of 2-methoxyethanol is boiled for 0.5 hours. The reaction mixture is cooled, diluted with 200 ml of chloroform, washed with water, dried and evaporated. The residue is crystallized from a 1:1 mixture of benzene and hexane to obtain 4.32 g (67%) of the aimed compound; m.p.: 120°–122° C.

Analysis: calculated for $C_{25}H_{26}F_3NO_2$: C: 69.90%, H: 6.10%, F: 13.27%, N: 3.26%; found: C: 69.71%, H: 6.15%, F: 13.17%, N: 3.35%.

EXAMPLE 3

Preparation of erythro-1,2-diphenyl-3,3,3-trifluoro-1-[4-(2-/bis-(2-hydroxyethyl)-amino/-ethoxy)-phenyl]-propane hydrochloride 8.98 g (20 mmoles) of erythro-1-[4-(2-bromoethoxy)-phenyl]-1,2-diphenyl-3,3,3-trifluoro-propane, prepared as described in Example 1, are dissolved in 42 g (400 mmoles) of diethanolamine, and the solution is heated at 100°–120° C. for 0.5 hours. The reaction mixture is processed as described in Example 2, and the residue is crystallized from a 1:2 mixture of an isopropanol solution of hydrochloric acid and ether. 5.98 g (58.7%) of the aimed compound are obtained; m.p.: 190°–195° C.

Analysis: calculated for $C_{27}H_{31}ClF_3NO_3$: C: 63.59%, H: 6.13%, Cl: 6.95%, F: 11.18%, N: 2.75%; found: C: 63.41%, H: 6.29%, Cl: 7.08%, F: 10.98%; N: 2.80%.

EXAMPLE 4

Preparation of erythro-1,2-diphenyl-3,3,3-trifluoro-1-[4-(2-/bis(2-chloroethyl)-amino/-ethoxy)-phenyl]-propane hydrochloride A mixture of 2.04 g (4 mmoles) of erythro-1,2-diphenyl-3,3,3-trifluoro-1-[4-(2-/bis(2-hydroxyethyl)-amino/-ethoxy)-phenyl]-propane-hydrochloride, prepared as described in Example 3, 10 ml of chloroform and 3 ml (40 mmoles) of thionyl chloride is boiled for 2 hours. The excess of thionyl chloride is evaporated in vacuo, and the residue is crystallized from a 1:2 mixture of methanol and ether. 1.16 g (53%) of the aimed compound are obtained; m.p.: 140°–143° C.

Analysis: calculated for $C_{27}H_{29}Cl_3F_3NO$: C: 59.30%, H: 5.34%, Cl: 19.45%, F: 10.42%, N: 2.56%; found: C: 59.16%, H: 5.53%, Cl: 19.32%, F: 10.60%, N: 2.62%.

EXAMPLE 5

Preparation of erythro-1-[4-(2-azidoethoxy)-phenyl]-1,2-diphenyl-3,3,3-trifluoro-propane A solution of 3.25 g (50 mmoles) of sodium azide in 11 ml of water is added to a solution of 11.2 g (25 mmoles) of erythro-1-[4-(2-bromoethoxy)-phenyl]-1,2-diphenyl-3,3,3-trifluoro-propane, prepared as described in Example 1, in 112 ml of 2-methoxyethanol, and the mixture is boiled for one hour. The reaction mixture is evaporated to dryness, 30 ml of toluene is added to the residue, and the mixture is evaporated again to remove the last traces of 2-methoxyethanol. The solid residue is triturated with water, filtered off and washed with water. The crude product is recrystallized twice from ethanol. 7.83 g (76%) of the aimed compound are obtained; m.p.: 144°–148° C.

Analysis: calculated for $C_{23}H_{20}F_3N_3O$: C: 67.14%, H: 4.90%, F: 13.85%, N: 10.21%; found: C: 67.35%, H: 5.15%, F: 13.94%, N: 10.06%.

EXAMPLE 6

Preparation of erythro-1-[4-(2-aminoethoxy)-phenyl]-1,2-diphenyl-3,3,3-trifluoro-propane 5.15 g (12.5 mmoles) of erythro-1-[4-(2-azidoethoxy)-phenyl]-1,2-diphenyl-3,3,3-trifluoro-propane, prepared as described in Example 5, are hydrogenated for about one hour in a mixture of 100 ml of methanol and 40 ml of tetrahydrofuran, in the presence of 0.6 g of a 5% palladium-on-carbon catalyst. The solution is evaporated and the residue is crystallized from hexane. 3.86 g (80.2%) of the desired compound are obtained; m.p.: 125°–127° C.

Analysis: calculated for $C_{23}H_{22}F_3NO$: C: 71.67%, H: 5.75%, F: 14.80%, N: 3.63%; found: C: 71.87%, H: 5.71%, F: 14.80%, N: 3.54%.

EXAMPLE 7

Preparation of (E)-1-[4-(2-azidoethoxy)-phenyl]-1,2-diphenyl-3,3,3-trifluoro-propene 9.83 g (22 mmoles) of (E)-1-[4-(2-bromoethoxy)-phenyl]-1,2-diphenyl-3,3,3-trifluoro-propene are dissolved in 100 ml of 2-methoxyethanol, a solution of 2.86 g (44 mmoles) of sodium azide in 10 ml of water is added, and the mixture is boiled for one hour. The reaction mixture is processed as described in Example 5, and the product is recrystallized twice from ethanol. 7.40 g (82%) of the aimed compound are obtained; m.p.: 73°–75° C.

Analysis: calculated for $C_{23}H_{18}F_3N_3O$: C: 67.47%, H: 4.43%, F: 13.92%, N: 10.27%; found: C: 67.61%, H: 4.45%, F: 13.77%, N: 10.11%.

The starting substance, (E)-1-[4-(2-bromoethoxy)-phenyl]-1,2-diphenyl-3,3,3-trifluoro-propene, is prepared as follows:

45.4 g (0.2 moles) of 2,3-dichloro-5,6-dicyano-1,4-benzoquinone (D. Walker et al.: J. Org. Chem. 30, 3240 (1965)) are added to a solution of 44.7 g (0.1 moles) of threo-1-[4-(2-bromoethoxy)-phenyl]-1,2-diphenyl-3,3,3-trifluoropropane, prepared as described in Example 1, in 225 ml of dry benzene, and the mixture is stirred and boiled for 30 hours. The reaction mixture is cooled and the separated 2,3-dichloro-5,6-dicyano-1,4-hydroquinone are filtered off. The filtrate is evaporated to dryness, the residue is admixed with 100 ml of chloroform, and the separated 2,3-dichloro-5,6-dicyano-1,4-benzoquinone is filtered off. The filtrate is diluted with 400 ml of chloroform, washed with a 10% aqueous sodium hydrocarbonate solution and then with water, dried and evaporated. The residue is crystallized from 220 ml of ethanol to obtain 34.4 g (77%) of a crude product melting at 110°–118° C. This crude product, which is a 4:1 mixture of the E and Z isomers, is recrystallized from 200 ml of ethanol. 29.5 g (66%) of the E isomer are obtained; m.p.: 118°–120° C.

Analysis: calculated for $C_{23}H_{18}BrF_3O$: C: 61.67%, H: 4.06%, Br: 17.87%, F: 12.74%; found: C: 61.80%, H: 4.15%, Br: 17.59%, F: 12.90%.

Spectral data: $\nu_{CH}$ 3060, 3020, 2920, 2900, 2850 $\nu_{C=C}$ 1590, 1495 $\gamma_{Ar}$ 815, 822, 758, 705 $\delta_{OCH_2}$=4.08 (t), 2H $\delta_{BrCH_2}$=3.46 (t), 2H $\delta_{Ar}$=6.4–7.4 (m), 14H.

The mother liquor obtained above is evaporated, and the residue is recrystallized several times from ethanol. 2.14 g (4.8%) of (Z)-1-[4-(2-bromoethoxy)-phenyl]-1,2-diphenyl-3,3,3-trifluoro-propene are obtained; m.p.: 135°–138° C.

Spectral data: $\nu_{CH}$ 3080, 3060, 3030, 2935, 2870 $\nu_{C=C}$ 1610, 1510 $\gamma_{Ar}$ 832, 770, 760, 715 $\delta_{OCH_2}$=4.28 (t), 2H $\delta_{BrCH_2}$=3.59 (t), 2H $\delta_{Ar}$=6.8–7.4 (m), 14H.

EXAMPLE 8

Preparation of (E)-1-[4-(2-aminoethoxy)-phenyl]-1,2-diphenyl-3,3,3-trifluoro-propene 7.40 g (18 mmoles) of (E)-1-[4-(2-azidoethoxy)-phenyl]-1,2-diphenyl-3,3,3-trifluoro-propene, prepared as described in Example 7, are dissolved in 100 ml of methanol, 0.70 g of a 5% palladium-on-carbon catalyst are added, and the mixture is hydrogenated for about one hour. The catalyst is filtered off, the solution is evaporated, and the residue is crystallized from hexane. 3.63 g (52.3%) of the aimed compound are obtained; m.p.: 71°–76° C.

Analysis: calculated for $C_{23}H_{20}F_3NO$: C: 72.05%, H: 5.26%, F: 14.87%, N: 3.65%; found: C: 72.36%, H: 5.30%, F: 14.88%, N: 3.52%.

EXAMPLE 9

Preparation of (E)-1,2-diphenyl-3,3,3-trifluoro-1-[4-(2-morpholinoethoxy)-phenyl]-propene A mixture of 3.34 g (7.5 mmoles) of (E)-1-[4-(2-bromoethoxy)-phenyl]-1,2-diphenyl-3,3,3-trifluoro-propene, prepared as described in Example 7, and 13 g of morpholine is boiled for one hour. The reaction mixture is processed as described in Example 1, and the crude product is crystallized from hexane. 2.80 g (82.4%) of the aimed compound are obtained; m.p.: 84°–89° C.

Analysis: calculated for $C_{27}H_{26}F_3NO_2$: C: 71.51%, H: 5.78%, F: 12.57%, N: 3.09%; found: C: 71.80%, H: 5.98%, F: 12.70%, N: 3.28%.

EXAMPLE 10

Preparation of
(E)-1,2-diphenyl-3,3,3-trifluoro-1-[4-(2-/4-methyl-piperazino/-ethoxy)-phenyl]propene 4.0 g of N-methylpiperazine are added to a solution of 4.47 g (10 mmoles) of (E)-1-[4-(2-bromoethoxy)-phenyl]-1,2-diphenyl-3,3,3-trifluoro-propene, prepared as described in Example 7, in 80 ml of dry ethanol, and the mixture is boiled for 6 hours. The reaction mixture is evaporated to dryness, and then one proceeds as described in Example 1. The product is crystallized from hexane. 3.45 g (74%) of the aimed compound are obtained; m.p.: 94°–97° C.

Analysis: calculated for $C_{28}H_{29}F_3N_2O$: C: 72.08%, H: 6.27%, F: 12.22%, N: 6.00%; found: C: 72.27%, H: 6.32%, F: 12.28%, N: 5.77%.

EXAMPLE 11

Preparation of
(E)-1,2-diphenyl-3,3,3-trifluoro-1-[4-(2-/4-(2-hydroxyethyl)-piperazino/-ethoxy)-phenyl]-propene A mixture of 1.79 g (4 mmoles) of (E)-1-[4-(2-bromoethoxy)-phenyl]-1,2-diphenyl-3,3,3-trifluoro-propene, prepared as described in Example 7, and 10.4 g of 1-(b 2-hydroxyethyl)piperazine is heated for one hour. The mixture is processed as described in Example 1, and the product is crystallized from hexane. 1.35 g (68%) of the aimed compound are obtained; m.p.: 79°–81° C.

Analysis: calculated for $C_{29}H_{31}F_3N_2O_2$: C: 70.14%, H: 6.29%, F: 11.48%, N: 5.64%; found: C: 70.15%, H: 5.65%, F: 11.36%, N: 5.48%.

EXAMPLE 12

Preparation of
(E)-1,2-diphenyl-3,3,3-trifluoro-1-[4-(2-/2-hydroxyethylamino/-ethoxy)-phenyl]-propene 6.71 g (15 mmoles) of (E)-1-[4-(2-bromoethoxy)-phenyl]-1,2-diphenyl-3,3,3-trifluoro-propene, prepared as described in Example 7, are dissolved in a mixture of 9.15 g of 2-aminoethanol and 15 ml of 2-methoxyethanol. The solution is boiled for 30 minutes, and then the mixture is processed as described in Example 2. The product is crystallized from a 1:1 mixture of ethyl acetate and hexane. 5.29 g (83%) of the aimed compound are obtained; m.p.: 96°–98° C.

Analysis: calculated for $C_{25}H_{24}F_3NO_2$: C: 70.24%, H: 5.66%, F: 13.33%, N: 3.28%; found: C: 70.42%, H: 5.80%, F: 13.39%, N: 3.23%.

EXAMPLE 13

Preparation of
(E)-1,2-diphenyl-3,3,3-trifluoro-1-[4-(2-/bis(2-hydroxyethyl)-amino/-ethoxy)-phenyl]-propene A solution of 7.15 g (16 mmoles) of (E)-1-[4-(2-bromoethoxy)-phenyl]-1,2-diphenyl-3,3,3-trifluoro-propene, prepared as described in Example 7, in 16.8 g of diethanolamine is heated at 120°–140° C. for 0.5 hours, and then one proceeds as described in Example 2. The product is crystallized from a 1:1 mixture of ethyl acetate and hexane. 5.66 g (75%) of the desired compound are obtained; m.p.: 113.5°–116° C.

Analysis: calculated for $C_{27}H_{28}F_3NO_3$: C: 68.78%, H: 5.99%, F: 12.09%; found: C: 68,75%, H: 5.78%, F: 12.13%.

EXAMPLE 14

Preparation of
(E)-1,2-diphenyl-3,3,3-trifluoro-1-[4-(2-/bis(2-chloroethyl)-amino/-ethoxy)-phenyl]-propene 3.6 ml (50 mmoles) of thionyl chloride are added to a solution of 2.36 g (5 mmoles) of (E)-1,2-diphenyl-3,3,3-trifluoro-1-[4-(2-/bis(2-hydroxyethyl)-amino/-ethoxy)-phenyl]-propene, prepared as described in Example 13, in 12 ml of chloroform, and the mixture is boiled for 2 hours. The excess of thionyl chloride is evaporated in vacuo, and the residue is crystallized from hexane. 1.90 g (74.7%) of the desired compound are obtained; m.p.: 74°–76° C.

Analysis: calculated for $C_{27}H_{26}Cl_2F_3NO$: C: 63.79%, H: 5.15%, Cl: 13.95%, F: 11.21%, N: 2.75%; found: C: 64.03%, H: 5.03%, Cl: 14.00%, F: 10.93%, N: 2.75%.

EXAMPLE 15

Preparation of
1-[4-(2-azidoethoxy)-phenyl]-1-phenyl-3,3,3-trifluoro-2-(4-fluorophenyl)-propene 11.63 g (25 mmoles) of 1-[4-(2-bromoethoxy)-phenyl]-1-phenyl-3,3,3-trifluoro-2-(4-fluorophenyl)-propene are converted into the azido derivative as described in Example 5. The product is crystallized from ethanol to obtain 8.54 g (80%) of the aimed compound; m.p.: 62°–64° C.

Analysis: calculated for $C_{23}H_{14}F_4N_3O$: C: 64.63%, H: 4.01%, F: 17.78%, N: 9.83%; found: C: 64.71%, H: 4.13%, F: 17.74%, N: 9.63%.

1-[4-(2-Bromoethoxy)-phenyl]-1-phenyl-3,3,3-trifluoro-2-(4-fluorophenyl)-propene, applied as starting substance, is prepared by the method of Examples 1 and 7 as follows:

4'-Fluoro-2,2,2-trifluoroacetophenone (F. E. Herkes et al.: J. Org. Chem. 32, 1311–18 (1967)) is reacted with benzyl-triphenyl-phosphonium chloride in the presence of an ethanol solution of sodium ethoxide. 1-Phenyl-3,3,3-trifluoro-2-(4-fluorophenyl)-propene is obtained with a yield of 91%; b.p.: 110°–114° C./0.2 mm Hg, m.p.: 43°–45° C.

Analysis: calculated for $C_{15}H_{10}F_4$: C: 67.67%, H: 3.79%, F: 28.54%; found: C: 67.83%, H: 3.90%, F: 28.33%.

This compound is hydrogenated in the presence of a palladium-on-carbon catalyst to obtain 1-phenyl-3,3,3-trifluoro-2-(4-fluorophenyl)-propane with a yield of 91.7%; b.p.: 100°–104° C./0.2 mm Hg; $n_D^{20}=1.4980$.

Analysis: calculated for $C_{15}H_{12}F_4$: C: 67.16%, H: 4.51%, F: 28.33%; found: C: 67.30%, H: 4.68%, F: 28.18%.

The above product is brominated in carbon tetrachloride, and the brominated compound is crystallized from ethanol. 1-Bromo-1-phenyl-3,3,3-trifluoro-2-(4-fluorophenyl)propane is obtained with a yield of 48.2%; m.p.: 144°–146° C.

Analysis: calculated for $C_{15}H_{11}BrF_4$: C: 51.90%, H: 3.19%, Br: 23.02%, F: 21.89%; found: C: 51.70%, H: 3.18%, Br: 23.06%, F: 22.03%.

The brominated compound is reacted with anisole in the presence of aluminium trichloride. The resulting 1-phenyl-3,3,3-trifluoro-2-(4-fluorophenyl)-1-(4-methoxyphenyl)-propane (mixture of isomers) is crystallized from isopropanol. Yield: 79.8%; m.p.: 152°–167° C.

Analysis: calculated for $C_{22}H_{18}F_4O$: C: 70.58%, H: 4.85%, F: 20.30%; found: C: 70.80%, H: 4.78%, F: 20.40%.

The above compound is heated with pyridine hydrochloride, and the resulting 1-phenyl-3,3,3-trifluoro-2-(4-fluorophenyl)-1-(4-hydroxyphenyl)-propane is reacted directly, without purification, with 1,2-dibromoethane in the presence of potassium hydroxide under heating. The resulting 1-[4-(2-bromoethoxy)-phenyl]-1-phenyl-3,3,3-trifluoro-2-(4-fluorophenyl)-propane is crystallized from isopropanol; 15 to 20 ml of isopropanol are applied for 1 g of the crude product. The first fraction, which is a mixture of isomers, melts at 170°–175° C.

Analysis: calculated for $C_{23}H_{19}BrF_4O$: C: 59.11%, H: 4.10%, Br: 17.10%, F: 16.26%; found: C: 58.88%, H: 4.21%, Br: 16.96%, F: 16.50%.

The mother liquor is evaporated to dryness, and the solid is recrystallized from benzene. 5 ml of benzene are applied for 1 g of the solid. The resulting second fraction, which is a mixture of isomers, melts at 100°–110° C.

Analysis: calculated for $C_{23}H_{19}BrF_4O$: C: 59.11%, H: 4.10%, Br: 17.10%, F: 16.26%; found: C: 58.96%, H: 4.07%, Br: 17.05%, F: 16.32%.

The above two fractions are combined and boiled with 2,3-dichloro-5,6-dicyano-1,4-benzoquinone for 25 hours as described in Example 7. The product is crystallized from ethanol. 1-[4-(2-Bromoethoxy)-phenyl]-1-phenyl-3,3,3-trifluoro-2-(4-fluorophenyl)-propene is obtained with a yield of 66.5%; m.p.: 115°–118° C.

Analysis: calculated for $C_{23}H_{17}BrF_4O$: C: 59.37%, H: 3.68%, Br: 17.17%, F: 16.33%; found: C: 59.48%, H: 3.87%, Br: 17.19%, F: 16.51%.

EXAMPLE 16

Preparation of
1-[4-(2-aminoethoxy)-phenyl]-1-phenyl-3,3,3-trifluoro-2-(4-fluorophenyl)-propene A solution of 8.54 g (20 mmoles) of 1-[4-(2-azidoethoxy)-phenyl]-1-phenyl-3,3,3-trifluoro-2-(4-fluorophenyl)propene, prepared as described in Example 15, in 170 ml of methanol is hydrogenated for about one hour in the presence of 0.9 g of a 5% palladium-on-carbon catalyst. The solution is evaporated and the product is crystallized from hexane. 4.51 g (56.4%) of the title compound are obtained; m.p.: 83°–89° C.

Analysis: calculated for $C_{23}H_{19}F_4NO$: C: 68.82%, H: 4.77%, F: 18.93%, N: 3.49%; found: C: 68.94%, H: 4.99%, F: 18.83%, N: 3.33%.

EXAMPLE 17

Preparation of
1-phenyl-3,3,3-trifluoro-2-(4-fluorophenyl)-1-[4-(2-morpholinoethoxy)-phenyl]-propene 3.25 g (7 mmoles) of 1-[4-(2-bromoethoxy)-phenyl]-1-phenyl-3,3,3-trifluoro-2-(4-fluorophenyl)-propene, prepared as described in Example 15, are reacted with morpholine as described in Example 1. The product is crystallized from hexane. 2.5 g (75.7%) of the aimed compound are obtained; m.p.: 67°–69° C.

Analysis: calculated for $C_{27}H_{25}F_4NO_2$: C: 68.78%, H: 5.35%, F: 16.12%, N: 2.97%; found: C: 68.62%, H: 5.94%, F: 16.40%, N: 3.14%.

EXAMPLE 18

Preparation of
2-phenyl-3,3,3-trifluoro-1-(4-fluorophenyl)-1-[4-(2-morpholinoethoxy)-phenyl]-propene 3.25 g (7 mmoles) of 1-[4-(2-bromoethoxy)-phenyl]-2-phenyl-3,3,3-trifluoro-1-(4-fluorophenyl)-propene are reacted with morpholine as described in Example 1. The product is crystallized from hexane. 3.03 g (92%) of the aimed compound are obtained; m.p.: 95°–96° C.

Analysis: calculated for $C_{27}H_{25}F_4NO_2$: C: 68.78%, H: 5.35%, F: 16.12%, N: 2.97%; found: C: 68,96%, H: 5.83%, F: 15.98%, N: 3.00%.

1-[4-(2-Bromoethoxy)-phenyl]-2-phenyl-3,3,3-trifluoro-1-(4-fluorophenyl)-propene, applied as starting substance, is prepared according to the method of Example 1 as follows:

2,2,2-Trifluoroacetophenone is reacted with triphenyl-(4-fluorobenzyl)-phosphonium chloride (R. A. Jones: Australian J. Chem. 18, 903–6 (1965) in ethanol in the presence of sodium ethoxide. 2-Phenyl-3,3,3-trifluoro-1-(4-fluorophenyl)-propene is obtained with a yield of 90%; b.p.: 105°–107° C./0.2 mm Hg, m.p.: 35°–41° C.

Analysis: calculated for $C_{15}H_{10}F_4$: C: 67.67%, H: 3.79%, F: 28.54%; found: C: 67.58%, H: 3.95%, F: 28.50%.

The above product is hydrogenated with a palladium-on-carbon catalyst to obtain 2-phenyl-3,3,3-trifluoro-1-(4-fluorophenyl)-propane with a yield of 94%; b.p.: 95°–100° C./0.3 mm Hg.

Analysis: calculated for $C_{15}H_{12}F_4$: C: 67.16%, H: 4.51%, F: 28.33%; found: C: 67.22%, H: 4.73%, F: 28.40%.

The obtained product is brominated in carbon tetrachloride, and the resulting 1-bromo-2-phenyl-3,3,3-trifluoro-1-(4-fluorophenyl)-propane is crystallized from ethanol. 3.5 ml of ethanol is applied for one g of the solid. The obtained first fraction, which is a mixture of isomers, melts at 143°–145° C.

Analysis: calculated for $C_{15}H_{11}BrF_4$: C: 51.90%, H: 3.19%, Br: 23.02%, F: 21.89%; found: C: 51.91%, H: 3.13%, Br: 22.92%, F: 22.06%.

The mother liquor is evaporated to about one-third of its original volume. The obtained second fraction, a mixture of isomers, melts at 69°–76° C.

Analysis: calculated for $C_{15}H_{11}BrF_4$: C: 51.90%, H: 3.19%, Br: 23.02%, F: 21.89%; found: C: 51.74%, H: 3.33%, Br: 23.08%, F: 22.02%.

The total yield amounts to 76%.

The above fractions are combined and reacted with anisole in the presence of aluminium trichloride. The resulting 2-phenyl-3,3,3-trifluoro-1-(4-fluorophenyl)-1-(4-methoxyphenyl)-propane is crystallized from ethanol. 4 mg of ethanol are applied for 1 g of the solid. The first fraction, a mixture of isomers, melts at 120°–127° C.

Analysis: calculated for $C_{22}H_{18}F_4O$: C: 70.58%, H: 4.85%, F: 20.30%; found: C: 70.81%, H: 5.01%, F: 20.35%.

The mother liquor is concentrated to about one-sixth of its original volume. The resulting second fraction, a mixture of isomers, melts at 84°–95° C.

Analysis: calculated for $C_{22}H_{18}F_4O$: C: 70.58%, H: 4.85%, F: 20.30%; found: C: 70.72%, H: 4.92%, F: 20.18%.

The total yield amounts to 78.8%.

The above fractions (mixtures of isomers) are combined and heated with pyridine hydrochloride. The resulting crude 2-phenyl-3,3,3-trifluoro-1-(4-fluorophenyl)-1-(4-hydroxyphenyl)-propane is reacted directly, without purification, with 1,2-dibromoethane in the presence of potassium hydroxide. The resulting 1-[4-(2-bromoethoxy)-phenyl]-2-phenyl-3,3,3-trifluoro-1-(4-fluorophenyl)-propane is crystallized from ethanol. 4 ml of ethanol are applied for 1 g of the solid. The first fraction, a mixture of isomers, melts at 119°–123° C.

Analysis: calculated for $C_{23}H_{19}BrF_4O$: C: 59.11%, H: 4.10%, Br: 17.10%, F: 16.26%; found: C: 59.30%, H: 4.16%, Br: 17.03%, F: 16.26%.

The mother liquor is evaporated to about one-half of its original volume. The obtained second fraction, a mixture of isomers, melts at 72°–74° C.

Analysis: calculated for $C_{23}H_{19}BrF_4O$: C: 59.11%, H: 4.10%, Br: 17.10%, F: 16.26%; found: C: 59.27%, H: 4.30%, Br: 17.13%, F: 16.36%.

The above fractions (mixtures of isomers) are combined and reacted with 2,3-dichloro-5,6-dicyano-1,4-benzoquinone in benzene under boiling, as described in Example 7. The reaction mixture is processed as described in Example 7, and the product is crystallized from isopropanol. 1-[4-(2-bromoethoxy)-phenyl]-2-phenyl-3,3,3-trifluoro-1-(4-fluorophenyl)-propene is obtained with a yield of 58.4%; m.p.: 142°–144° C.

Analysis: calculated for $C_{23}H_{17}BrF_4O$: C: 59.37%, H: 3.68%, Br: 17.17%, F: 16.33%; found: C: 59.20%, H: 3.90%, Br: 17.36%, F: 16.20%.

EXAMPLE 19

Preparation of
1-[4-(2-dimethylamino-ethoxy)-phenyl]-1-phenyl-3,3,3-trifluoro-2-(4-methoxyphenyl)-propene 0.39 g (0,017 g.-atoms) of sodium are dissolved in 3.12 g (35 mmoles) of 2-dimethylamino-ethanol. 3.15 g (8.5 mmoles) of 1-phenyl-3,3,3-trifluoro-1-(4-fluorophenyl)-2-(4-methoxyphenyl)-propene are added to the solution, and the mixture is heated at 150°–155° C. for one hour. The reaction mixture is cooled, diluted with 200 ml of ether, washed with water until neutral, dried and evaporated. The residue is dissolved in 30 ml of hexane, the solution is filtered, and the filtrate is evaporated. 3.39 g (90%) of 1-[4-(2-dimethylamino-ethoxy)-phenyl]-1-phenyl-3,3,3-trifluoro-2-(4-methoxyphenyl)-propene are obtained as a resinous substance; the product is a 3:4 mixture of the (Z) and (E) isomers.

Analysis: calculated for $C_{26}H_{26}F_3NO_2$: C: 70.73%, H: 5.94%, F: 12.91%, N: 3.17%; found: C: 70.65%, H: 6.07%, F: 13.05%, N: 3.26%.

1-Phenyl-3,3,3-trifluoro-1-(4-fluorophenyl)-2-(4-methoxyphenyl)-propene, applied as starting substance, is prepared according to the method of Example 1 as follows:

4'-Methoxy-2,2,2-trifluoroacetophenone (R. Fuchs: J. Org. Chem. 22, 993–994 (1957)) is reacted with triphenyl(4-fluorobenzyl)-phosphonium chloride (see Example 18) in ethanol in the presence of sodium ethoxide. 3,3,3-Trifluoro-1-(4-fluorophenyl)-2-(4-methoxyphenyl)-propene is obtained with a yield of 87%; b.p.: 138°–142° C./0.5 mm Hg.

Analysis: calculated for $C_{16}H_{12}F_4O$: C: 64.86%, H: 4.08%, F: 25.65%; found: C: 65.03%, H: 4.27%, F: 25.40%.

The above compound is hydrogenated in the presence of a palladium-on-carbon catalyst to obtain 3,3,3-trifluoro-1-(4-fluorophenyl)-2-(4-methoxyphenyl)-propane with a yield of 93%; b.p.: 134°–136° C./0.4 mm Hg, $n_D^{20}=1.5070$.

Analysis: calculated for $C_{16}H_{14}F_4O$: C: 64.43%, H: 4.73%, F: 25.48%; found: C: 64.60%, H: 4.85%, F: 25.35%.

The above compound is brominated in carbon tetrachloride, and the product is crystallized from hexane. 1-Bromo-3,3,3-trifluoro-1-(4-fluorophenyl)-2-(4-methoxyphenyl)-propane (mixture of isomers) is obtained with a yield of 49%; m.p.: 73°–94° C.

Analysis: calculated for $C_{16}H_{13}BrF_4O$: C: 50.95%, H: 3.47%, Br: 21.19%, F: 20.15%; found: C: 50.82%, H: 3.60%, Br: 21.11%, F: 20.30%.

The above compound is reacted with benzene in the presence of aluminium trichloride, and the resulting 1-phenyl-3,3,3-trifluoro-1-(4-fluorophenyl)-2-(4-methoxyphenyl)-propane is crystallized from isopropanol. 5 ml of isopropanol are applied for 1 g of the solid. The first fraction, a mixture of isomers, melts at 126°–145° C.

Analysis: calculated for $C_{22}H_{18}F_4O$: C: 70.58%, H: 4.85%, F: 20.30%; found: C: 70.77%, H: 4.67%, F: 20.45%.

The mother liquor is evaporated to one-fifth of its original volume. The resulting second fraction, a mixture of isomers, melts at 102°–110° C.

Analysis: calculated for $C_{22}H_{18}F_4O$: C: 70.58%, H: 4.85%, F: 20.30%; found: C: 70.65%, H: 4.80%, F: 20.51%.

The above two fractions are combined and reacted with 2,3-dichloro-5,6-dicyano-1,4-benzoquinone as described in Example 7 for 120 hours under boiling. The product is crystallized from isopropanol. 1-Phenyl-3,3,3-trifluoro-1-(4-fluorophenyl)-2-(4-methoxyphenyl)-propane is obtained with a yield of 62%; m.p.: 113°–120° C.

Analysis: calculated for $C_{22}H_{16}F_4O$: C: 70.96%, H: 4.33%, F: 20.41%; found: C: 71.17%, H: 4.48%, F: 20.70%.

EXAMPLE 20

Preparation of
1[4-(2-dimethylamino-ethoxy)-phenyl]-2-phenyl-3,3,3-trifluoro-1-(4-methoxyphenyl)-propene 0.46 g (0.02 g.-atoms) of sodium are dissolved in 4.5 g (50 mmoles) of 2-dimethylamino-ethanol. 3.72 g (10 mmoles) of 2-phenyl-3,3,3-trifluoro-1-(4-fluorophenyl)-1-(4-methoxyphenyl)-propene are added to the solution, the mixture is heated at 150°–155° C. for one hour, and then processed as described in Example 19. 3.95 g (89.6%) of 1-[4-(2-dimethylamino-ethoxy)-phenyl]-2-phenyl-3,3,3-trifluoro-1-(4-methoxyphenyl)propene are obtained as a resinous substance; the product is a 9:1 mixture of the (Z) and (E) isomers.

Analysis: calculated for $C_{26}H_{26}F_3NO_2$: C: 70.73%, H: 5.94%, F: 12.91%, N: 3.17%; found: C: 70.50%, H: 6.11%, F: 12.73%, N: 2.91%.

2-Phenyl-3,3,3-trifluoro-1-(4-fluorophenyl)-1-(4-methoxyphenyl)-propene, applied as starting substance, is prepared as follows:

2-Phenyl-3,3,3-trifluoro-1-(4-fluorophenyl)-1-(4-methoxyphenyl)-propane, prepared as described in Example 18, is reacted with 2,3-dichloro-5,6-dicyano-1,4-benzoquinone under boiling for 8 hours as described in Example 7. The reaction mixture is processed, and the product is crystallized from ethanol. 2-Phenyl-3,3,3-trifluoro-1-(4-fluorophenyl)-1-(4-methoxyphenyl)-propene is obtained with a yield of 51%; m.p.: 52°–56° C.

Analysis: calculated for $C_{22}H_{16}F_4O$: C: 70.96%, H: 4.33%, F: 20.41%; found: C: 71.22%, H: 4.51%, F: 20.54%.

EXAMPLE 21

Preparation of
1-[4-(2-dimethylamino-ethoxy)-phenyl]-1-phenyl-3,3,3-trifluoro-2-(4-hydroxyphenyl)-propene hydrochloride 0.76 g (1.62 mmoles) of 1-[4-(2-dimethylamino-ethoxy)-phenyl]-1-phenyl-3,3,3-trifluoro-2-[4-(methoxy-methoxy)-phenyl]-propene are dissolved in 8 ml of a 1% methanolic hydrochloric acid. The solution is heated for 0.5 hour, then evaporated, and the product is crystallized from isopropanol. 0.56 g (74%) of the aimed compound is obtained; m.p.: 196°–220° C.

Analysis: calculated for $C_{25}H_{25}ClF_3NO_2$: C: 64.72%, H: 5.43%, Cl: 7.64%, F: 12.29%, N: 3.02%; found: C: 64.51%, H: 5.31%, Cl: 7.49%, F: 12.51%, N: 2.84%.

1-[4-(2-Dimethylamino-ethoxy)-phenyl]-1-phenyl-3,3,3-trifluoro-2-[4-(methoxy-methoxy)-phenyl]-propene, applied as starting substance, is prepared as follows:

A mixture of 18.72 g (50 mmoles) of 1-phenyl-3,3,3-trifluoro-1-(4-fluorophenyl)-2-(4-methoxyphenyl)-propane, prepared as described in Example 19, and 56 g of pyridine hydrochloride is heated at 200° C. for 3 hours, and then processed as described in Example 1. The resulting crude 1-phenyl-3,3,3-trifluoro-1-(4-fluorophenyl)-2-(4-hydroxyphenyl)-propane is dissolved in 70 ml of benzene, then 6.44 g (80 mmoles) of chloromethylether and 6 g (300 mmoles) of powdered sodium hydroxide are added, and the mixture is boiled for one hour. The reaction mixture is diluted with 100 ml of benzene, washed until neutral with a 20% aqueous ammonium chloride solution, dried and evaporated. The residue is crystallized from isopropanol. 12.54 g (62%) of 1-phenyl-3,3,3-trifluoro-1-(4-fluorophenyl)-2-[4-(methoxy-methoxy)-phenyl]-propane are obtained; m.p.: 96.5°–99° C.

Analysis: calculated for $C_{23}H_{20}F_4O_2$: C: 68.31%, H: 4.99%, F: 18.79%; found: C: 68.45%, H: 5.07%, F: 18.73%.

12.13 g (30 mmoles) of the above compound are boiled with 13.62 g (60 mmoles) of 2,3-dichloro-5,6-dicyano-1,4-benzoquinone in benzene for 120 hours. The reaction mixture is processed as described in Example 7, and the product is crystallized from isopropanol. 3.38 g (28%) of 1-phenyl-3,3,3-trifluoro-1-(4-fluorophenyl)-2-[4-(methoxy-methoxy)-phenyl]-propane are obtained; m.p.: 85°–88° C.

Analysis: calculated for $C_{23}H_{18}F_4O_2$: C: 68.65%, H: 4.51%, F: 18.89%; found: C: 68,78%, H: 4.65%, F: 18.81%.

0.09 g (0.004 g.-atoms) of sodium are dissolved in 0.89 g (10 mmoles) of 2-dimethylamino-ethanol. 0.80 g (2mmoles) of the above compound are added, and the mixture is reacted as described in Example 19. 0.76 g (80.6%) of 1-[4-(2-dimethylamino-ethoxy)-phenyl]-1-phenyl-3,3,3-trifluoro-2-[4-(methoxy-methoxy)-phenyl]-propene is obtained as a resinous substance, which can be utilized in the subsequent step without purification.

EXAMPLE 22

Preparation of
1-[4-(2-dimethylamino-ethoxy)-phenyl]-2-phenyl-3,3,3-trifluoro-1-(4-hydroxyphenyl)-propene 2.06 g (4.56 mmoles) of 1-(4-benzyloxyphenyl)-1-[4-(2-dimethylamino-ethoxy)-phenyl]-2-phenyl-3,3,3-trifluoropropene are dissolved in 45 ml of acetic acid and hydrogenated in the presence of 0.5 g of a 10% palladium-on-carbon catalyst. The solution is evaporated and the radius is crystallized from ether. 0.77 g (39.5%) of the aimed compound is obtained; m.p.: 149°–155° C.

Analysis: calculated for $C_{25}H_{24}F_3NO_2$: C: 70.24%, H: 5.66%, F: 13.33%, N: 3.28%; found: C: 69.92%, H: 6.12%, F: 13.28%, N: 3.38%.

1-(4-Benzyloxy-phenyl)-1-[4-(2-dimethylamino-ethoxy)-phenyl]-2-phenyl-3,3,3-trifluoro-propene, applied as starting substance, is prepared as follows:

2-Phenyl-3,3,3-trifluoro-1-(4-fluorophenyl)-1-(4-methoxyphenyl)-propane, prepared as described in Example 18, is reacted with pyridine hydrochloride as described in Example 1, and the resulting 2-phenyl-3,3,3-trifluoro-1-(4-fluorophenyl)-1-(4-hydroxyphenyl)-propane is reacted with benzyl chloride is ethanol solution, in the presence of sodium hydroxide. The product is crystallized from ethanol. 1-(4-Benzyloxyphenyl)-2-phenyl-3,3,3-trifluoro-1-(4-fluorophenyl)-propane is obtained with a yield of 64%; m.p.: 104°–125° C.

Analysis: calculated for $C_{28}H_{22}F_4O$: C: 74.65%, H: 4.92%, F: 16.87%; found: C: 74.82%, H: 4.68%, F: 16.92%.

This compound is reacted with 2,3-dichloro-5,6-dicyano-1,4-benzoquinone for 6 hours as described in Example 7. The obtained product is crystallized from ethanol. 1-(4-Benzyloxyphenyl)-2-phenyl-3,3,3-trifluoro-1-(4-fluorophenyl)-propane is obtained with a yield of 24.5%; m.p.: 111°–114° C.

Analysis: calculated for $C_{28}H_{20}F_4O$: C: 74.99%, H: 4.50%, F: 16.94%; found: C: 75.17%, H: 4.81%, F: 16.91%.

This compound is reacted with a solution of 2-dimethylamino-ethanol and sodium as described in Example 19. The resulting 1-(4-benzyloxyphenyl)-1-[4-(2-dimethylaminoethoxy)-phenyl]-2-phenyl-3,3,3-trifluoro-propene can be applied in the subsequent step without purification.

EXAMPLE 23

Preparation of
threo-1,2-diphenyl-3,3,3-trifluoro-1-[4-(methoxy-methoxy)-phenyl]-propane 2 g (50 mmoles) of sodium hydroxide and 4 g (50 mmoles) of chloromethyl ether are added to a solution of 10.26 g (30 mmoles) of threo-1,2-diphenyl-3,3,3-trifluoro-1-(4-hydroxyphenyl)-propane, prepared as described in Example 1, in 40 ml of benzene, and the mixture is boiled for one hour. The reaction mixture is diluted with 100 ml of benzene, washed with a 20% aqueous ammonium chloride solution, dried and evaporated. The residue is crystallized from isopropanol. 7.45 g (64.2%) of the aimed compound are obtained; m.p.: 100°–103° C.

Analysis: calculated for $C_{23}H_{21}F_3O_2$: C: 71.49%, H: 5.48%, F: 14.75%; found: C: 71.72%, H: 5.71%, F: 14.91%.

EXAMPLE 24

Preparation of
threo-1-[4-(2,3-epoxypropoxy)-phenyl]-1,2-diphenyl-3,3,3-trifluoro-propane 0.48 g (12 mmoles) of sodium hydroxide and 9.2 g (100 mmoles) of 1,2-epoxy-3-chloropropane are added to a solution of 3.42 g (10 mmoles) of threo-1,2-diphenyl-3,3,3-trifluoro-1-(4-hydroxyphenyl)-propane, prepared as described in Example 1, in 40 ml of ethanol, and the mixture is boiled for one hour. The reaction mixture is evaporated, n-butanol is added to the residue, and the mixture is again evaporated. The residue is diluted with 30 ml of dichloromethane, washed with water, dried and evaporated. The residue is crystallized from methanol. 2.85 g (71.6%) of the aimed compound are obtained; m.p.: 113°–116° C.

Analysis: calculated for $C_{24}H_{21}F_3O_2$: C: 72.35%, H: 5.31%, F: 14.31%; found: C: 72.26%, H: 5.14%, F: 14.47%.

EXAMPLE 25

Preparation of
erythro-1-[4-(2,3-epoxypropoxy)-phenyl]-1,2-diphenyl-3,3,3-trifluoro-propane 4.28 g (12.5 mmoles) or erythro-1,2-diphenyl-3,3,3-trifluoro-1-(4-hydroxyphenyl)-propane, prepared as described in Example 1, are reacted with 1,2-epoxy-3-chloropropane in the presence of sodium hydroxide as described in Example 24. The product is recrystallized twice from methanol. 2.18 g (44%) of the aimed compound are obtained; m.p.: 115°–118° C.

Analysis: calculated for $C_{24}H_{21}F_3O_2$: C: 72.35%, H: 5.31%, F: 14.31%; found: C: 72.18%, H: 5.46%, F: 14.37%.

EXAMPLE 26

Preparation of
(E)-1-[4-(2,3-eipxoypropoxy)-phenyl]-1,2-diphenyl-3,3,3-trifluoro-propene 0.29 g (12 mmoles) of sodium hydride are added to a solution of 3.40 g (10 mmoles) of (E)-1,2-diphenyl-3,3,3-trifluoro-1-(4-hydroxyphenyl)-propene in 30 ml of dry benzene, and the mixture is stirred for 0.5 hours. Thereafter 1.39 g (15 mmoles) of 1,2-epoxy-3-chloropropane are introduced, and the mixture is heated for 5 hours. The reaction mixture is diluted with 70 ml of benzene, washed with water, dried, evaporated, and the residue is crystallized from metahnol. 2.46 g (62%) of the aimed compound are obtained; m.p.: 73.5°–76° C.

Analysis: calculated for $C_{24}H_{19}F_3O$: C: 72.72%, H: 4.83%, F: 14.38%; found: C: 72.89%, H: 4.88%, F: 14.61%.

(E)-1,2-Diphenyl-3,3,3-trifluoro-1-(4-hydroxyphenyl)-propene, applied as starting substance, is prepared as follows: 2.2 g (55 mmoles) of sodium hydroxide and 6.9 g (55 mmoles) of benzyl chloride are added to a solution of 15.4 g (45 mmoles) of 1,2-diphenyl-3,3,3-trifluoro-1-(4-hydroxyphenyl)-propane, prepared as described in Example 1, in 75 ml of ethanol, and the resulting mixture is boiled for one hour. The reaction mixture is diluted with 300 ml of water, neutralized with an 1 n aqueous solution of hydrochloric acid, and extracted with 200 ml of chloroform. The organic phase is washed with water, dried and evaporated. The residue is crystallized from ethanol. 17 g (86.6%) of the product are obtained; m.p.: 94°–118° C.

Analysis: calculated for $C_{28}H_{23}F_3O$: C: 77.76%, H: 5.36%, F: 13.18%; found: C: 77.95%, H: 5.44%, F: 13.42%.

A mixture of 16.42 g (38 mmoles) of the above product, 17.25 g (76 mmoles) of 2,3-dichloro-5,6-dicyano-1,4-benzoquinone and 80 ml of benzene is boiled for 2 hours, and then it is processed as described in Example 7. The product is crystallized from ethanol. 6.21 g (38%) of (E)-1-(4-benzyloxyphenyl)-1,2-diphenyl-3,3,3-trifluoro-propene are obtained; m.p.: 128°–129° C.

Analysis: calculated for $C_{28}H_{21}F_3O$: C: 78.13%, H: 4.92%, F: 13.24%; found: C: 78.34%, H: 5.10%, F: 13.24%.

The NMR spectrum of the product confirms the structure.

6.02 g (14 mmoles) of the above product are hydrogenated in a 1:1 mixture of methanol and tetrahydrofuran in the presence of a 5% palladium-on-carbon catalyst. The solution is evaporated and the residue is crystallized from a 1:2 mixture of chloroform and hexane. 3.50 g (73.5%) of (E)-1,2-diphenyl-3,3,3-trifluoro-1-(4-hydroxyphenyl)-propene are obtained; m.p.: 113°–120° C.

Analysis: calculated for $C_{21}H_{15}F_3O$: C: 74.11%, H: 4.44%, F: 16.75%; found: C: 74.17%, H: 4.85%, F: 16.53%.

EXAMPLE 27

Preparation of
1-[4-(2,3-epoxypropoxy)-phenyl]-1-phenyl-3,3,3-trifluoro-2-(4-chlorophenyl)-propane 0.8 g (20 mmoles) of sodium hydroxide and 14.8 g (160 mmoles) of 1,2-epoxy-3-chloropropane are added to a solution of 6.03 g (16 mmoles) of 1-phenyl-3,3,3-trifluoro-1-(4-hydroxyphenyl)-2-(4-chlorophenyl)-propane in 60 ml of methanol. The mixture is boiled for 2 hours and then processed as described in Example 25. The product is crystallized from methanol. 4.44 g (64%) of the aimed compound are obtained; m.p.: 141°–144° C.

Analysis: calculated for $C_{24}H_{20}ClF_3O_2$: C: 66.59%, H: 4.66%, Cl: 8.19%, F: 13.17%; found: C: 66.71%, H: 5.05%, Cl: 8.35%, F: 13.29%.

1-Phenyl-3,3,3-trifluoro-1-(4-hydroxyphenyl)-2-(4-chlorophenyl)-propane, applied as starting substance, is prepared by the method of Example 1 as follows:

4'-Chloro-2,2,2-trifluoroacetophenone (R. Fuchs, J. Org. Chem. 22, 993–994 (1957)) is reacted with benzyltriphenylphosphonium chloride in the presence of an ethanolic solution of sodium ethoxide. The product is crystallized from hexane. 1-Phenyl-3,3,3-trifluoro-2-(4-chlorophenyl)-propene is obtained with a yield of 68%; m.p.: 63–66° C.

Analysis: calculated for $C_{15}H_{10}ClF_3$: C: 63.73%, H: 3.57%, Cl: 12.54%, F: 20.16%; found: C: 63.91%, H: 3.81%, Cl: 12.37%, F: 20.03%.

The above product is hydrogenated in acetic acid in the presence of a 10% palladium-on-carbon catalyst to obtain 1-phenyl-3,3,3-trifluoro-2-(4-chlorophenyl)-propane with a yield of 86%; b.p.: 118°–120° C./0.4 mm Hg, $n_D^{20} = 1.5230$.

Analysis: calculated for $C_{15}H_{12}ClF_3$: C: 63.28%, H: 4.25%, Cl: 12.45%, F: 20.02%; found: C: 63.51%, H: 4.40%, Cl: 12.38%, F: 19.93%.

The above product is brominated in carbon tetrachloride, and the bromine derivative is crystallized from hexane. 1-Bromo-1-phenyl-3,3,3-trifluoro-2-(4-chlorophenyl)-propane is obtained with a yield of 45.3%; m.p.: 143°–146° C.

Analysis: calculated for $C_{15}H_{11}BrClF_3$: C: 49.55%, H: 3.05%, Br: 21.98%, Cl: 9.75%, F: 15.68%; found: C: 49.68%, H: 3.15%, Br: 22.03%, Cl: 9.71%, F: 15.53%.

The above product is reacted with anisole in the presence of aluminium trichloride, and the resulting 1-phenyl-3,3,3-trifluoro-2-(4-chlorophenyl)-1-(4-methoxyphenyl)-propane is crystallized from isopropanol. Yield: 66%; m.p.: 164°–171° C.

Analysis: calculated for $C_{22}H_{18}ClF_3O$: C: 67.61%, H: 4.64%, Cl: 9.07%, F: 14.58%; found: C: 67.75%, H: 4.70%, Cl: 9.01%, F: 14.45%.

The above product is reacted with pyridine hydrochloride to obtain 1-phenyl-3,3,3-trifluoro-1-(4-hydroxyphenyl)-2-(4-chlorophenyl)-propane, which is utilized in the subsequent step without purification.

EXAMPLE 28

Preparation of threo-1-[4-(2-dimethylamino-ethoxy)-phenyl]-1,2-diphenyl-3,3,3-trifluoro-propane hydrochloride A mixture of 6.84 g (20 mmoles) of threo-1,2-diphenyl-3,3,3-trifluoro-1-(4-hydroxyphenyl)-propane, prepared as described in Example 1, 0.6 g (24 mmoles) of sodium hydride and 60 ml of dry xylene is stirred for 0.5 hours. 7.2 ml of a 4.16 molar xylene solution of 2-dimethylaminoethyl chloride (=30 mmoles) are introduced, and the reaction mixture is heated for 2 hours. The mixture is evaporated, the residue is admixed with 10 ml of a 9.36% methanolic hydrochloric acid, and the solvent is evaporated. The residue is crystallized from isopropanol. 5.76 g (64%) of the aimed compound are obtained; m.p.: 229°–231° C.

Analysis: calculated for $C_{25}H_{27}ClF_3NO$: C: 66.74%, H: 6.05%, Cl: 7.88%, F: 12.67%, N: 3.11%; found: C: 66.47%, H: 6.03%, Cl: 7.96%, F: 12.86%, N: 3.00%.

EXAMPLE 29

Preparation of threo-1,2-diphenyl-3,3,3-trifluoro-1-[4-(2-morpholinoethoxy)-phenyl]-propane 3.42 g (10 mmoles) of threo-1,2-diphenyl-3,3,3-trifluoro-1-(4-hydroxyphenyl)-propane, prepared as described in Example 1, are reacted in xylene with sodium hydride and then with 2-chloroethyl-morpholine as described in Example 28. The product is crystallized from hexane. 3.12 g (68.5%) of the desired compound are obtained; m.p.: 87°–89° C.

Analysis: calculated for $C_{27}HP_{28}F_3NO_2$: C: 71.19%, H: 6.20%, F: 12.51%, N: 3.08%; found: C: 71.41%, H: 6.48%, F: 12.35%, N: 3.01%.

EXAMPLE 30

Preparation of (E)-1,2-diphenyl-3,3,3-trifluoro-1-[4-(2-pyrrolidinoethoxy)-phenyl]-propene 2.72 g (8 mmoles) of (E)-1,2-diphenyl-3,3,3-trifluoro-1-(4-hydroxyphenyl)-propene, prepared as described in Example 26, are reacted in xylene with sodium hydride and then with 2-chloroethyl-pyrrolidine as described in Example 26. The product is crystallized from hexane. 2.15 g (61.4%) of the desired compound are obtained; m.p.: 84.5°–86° C.

Analysis: calculated for $C_{27}H_{26}F_3NO$: C: 74.12%, H: 5.99%, F: 13.03%, N: 3.20%; found: C: 74.40%, H: 6.11%, F: 13.15%, N: 3.15%.

EXAMPLE 31

Preparation of 1-[4-(2-dimethylamino-ethoxy)-phenyl]-3,3,3-trifluoro-1,2-bis-(4-methoxyphenyl)-propene 0.46 g (0.02 g.-atoms) of sodium are dissolved in 3.56 g (40 mmoles) of 2-dimethylamino-ethanol, 4.02 g (10 mmoles) of 1-(4-fluorophenyl)-3,3,3-trifluoro-1,2-bis-(4-methoxyphenyl)-propene are added, and the mixture is heated at 170° C. for one hour. The reaction mixture is cooled, diluted with 200 ml of ether, washed with water until neutral, dried and then evaporated. The residue is recrystallized from 45 ml of hexane. 3.43 g (73%) of the aimed compound are obtained; m.p.: 77°–79° C.

Analysis: calculated for $C_{27}H_{28}F_3NO_3$: C: 68.92%, H: 5.78%, F: 12.11%, N: 2.98%; found: C: 68.97%, H: 5.85%, F: 12.10%, N: 2.99%.

1-(4-Fluorophenyl)-3,3,3-trifluoro-1,2-bis (4-methoxyphenyl)-propane, applied as starting substance, is prepared as follows:

20 g (0.15 moles) of anhydrous aluminium trichloride are added to a solution of 56.6 g (0.15 moles) of 1-bromo-3,3,3-trifluoro-1-(4-fluorophenyl)-2-(4-methoxyphenyl)-propane, prepared as described in Example 19, in 570 ml of anisol at 6° C. under stirring. The reaction mixture is allowed to stand at room temperature overnight, then it is poured into a mixture of 600 g of crushed ice and 100 ml of a 36% aqueous hydrochloric acid, and the resulting mixture is extracted with 500 ml of chloroform. The organic solution is washed with aqueous sodium hydrocarbonate solution and water, dried, and the solvent is evaporated. The dry residue is crystallized from 240 ml of isopropanol to obtain 34.6 g (57%) of 1-(4-fluorophenyl)-3,3,3-trifluoro-1,2-bis (4-methoxyphenyl)-propane; m.p.: 132°–135° C.

Analysis: calculated for $C_{23}H_{20}F_4O_2$: C: 68.31%, H: 4.99%, F: 18.79%; found: C: 68.45%, H: 5.14%, F: 18.63%.

13.62 g (60 mmoles) of 2,3-dichloro-5,6-dicyano-1,4-benzoquinone are added to a solution of 12.13 g (30 mmoles) of the above product in 60 ml of dry benzene, and the mixture is stirred and boiled for 16 hours. Thereafter one proceeds as described in Example 7. The crude product is crystallized from 40 ml of isopropanol to obtain 8.75 g (72.5%) of 1-(4-fluorophenyl)-3,3,3-trifluoro-1,2-bis (4-methoxyphenyl)-propene; m.p.: 75°–77° C.

Analysis: calculated for $C_{23}H_{18}F_4O_2$: C: 68.65%, H: 4.51%, F: 18.89%; found: C: 69.07%, H: 4.57%, F: 19.03%.

EXAMPLE 32

Preparation of 1-[4-(2-dimethylamino-ethoxy)-phenyl]-3,3,3-trifluoro-1,2-bis (4-hydroxyphenyl)-propene-hydrochloride 10 ml of a 9% methanolic hydrochloric acid are added to a solution of 4.0 g (7.47 mmoles) of 1-[4-(2-dimethylaminoethoxy)-phenyl]-3,3,3-trifluoro-1,2-bis-(4-methoxymethoxyphenyl)-propene in 40 ml of methanol, and the mixture is boiled for one hour. The solution is evaporated to dryness, and the residue is crystallized from ethanol. 2.67 g (74.4%) of the desired compound are obtained; m.p.: 256°–262° C.

Analysis: calculated for $C_{25}H_{25}ClF_3NO_3$: C: 62.57%, H: 5.25%, Cl: 7.39%, F: 11.88%, N: 2.92%; found: C: 62.61%, H: 5.52%, Cl: 7.62%, F: 11.69%, N: 2.81%.

1-[4-(2-Dimethylamino-ethoxy)-phenyl]-3,3,3-trifluoro-1,2-bis (4-methoxymethoxy-phenyl)-propene, applied as starting substance, is prepared as follows:

A mixture of 18.72 g (46 mmoles) of 1-(4-fluorophenyl)-3,3,3-trifluoro-1,2,-bis-(4-methoxyphenyl)-propane, prepared as described in Example 31, and 76 g of pyridine hydrochloride is heated at 200°–210° C. for 3 hours. The mixture is cooled, diluted with 200 ml of chloroform and washed with water until neutral. The solution is dried and evaporated. The resulting 17.7 g of 1-(4-fluorophenyl)-3,3,3-trifluoro-1,2-bis-(4-hydroxyphenyl)-propane are dissolved as such, without purification, in 200 ml of benzene. 11.1 g (138 mmoles) of chloromethyl ether and 10 g (275 mmoles) of powdered sodium hydroxide are added to the solution, and the mixture is boiled for one hour. The mixture is diluted with 100 ml of benzene, washed with a 20% aqueous ammonium chloride solution until neutral, dried and evaporated. The residue is crystallized from isopropanol. 15.63 g (73%) of 1-(4-fluorophenyl)-3,3,3-trifluoro-1,2-bis-(4-methoxy-methoxy-phenyl)-propane are obtained; m.p.: 106°–107° C.

Analysis: calculated for $C_{25}H_{24}F_4O_4$: C: 64.65%, H: 5.21%, F: 16.36%; found: C: 64.60%, H: 5.52%, F: 16.47%.

5.86 g (26 mmoles) of 2,3-dichloro-5,6-dicyano-1,4-benzoquinone are added to a solution of 6.0 g (12.9 mmoles) of 1-(4-fluorophenyl)-3,3,3-trifluoro-1,2-bis-(4-methoxy-methoxy-phenyl)-propane in 30 ml of dry benzene. The mixture is boiled for 28 hours and then processed as described in Example 7. The product is crystallized from isopropanol. 4.42 g (74%) of the aimed compound are obtained; m.p.: 73°–74° C.

Analysis: calculated for $C_{25}H_{22}F_4O_4$: C: 64.93%, H: 4.80%, F: 16.43%; found: C: 64.67%, H: 4.98%, F: 16.49%.

3.0 g (6.5 mmoles) of the above product are added to a solution of 0.35 g (0.015 g.-atoms) of sodium in 2.67 g (30 mmoles) of dimethylamino-ethanol, and the mixture is treated as described in Example 19. 3.97 g (100%) of 1-[4-(2-dimethylamino-ethoxy)-phenyl]-3,3,3-trifluoro-1,2-bis-(4-methoxy-methoxy)-phenyl-propene are obtained as a resinous substance. This product is utilized in the subsequent step without purification.

EXAMPLE 33

Preparation of
2-phenyl-3,3,3-trifluoro-1-(4-hydroxyphenyl)-1-[4-(2-morpholinoethoxy)-phenyl]-propene 10 ml of a 9% methanolic hydrochloric acid are added to a solution of 3.08 g (6 mmoles) of 2-phenyl-3,3,3-trifluoro-1-[4-(2-morpholinoethoxy)-phenyl]-1-(4-methoxymethoxy-phenyl)-propene in 40 ml of methanol, and the mixture is boiled for one hour. The solution is rendered alkaline with 1.5 ml of a 10 n sodium hydroxide solution and then evaporated. The residue is dissolved in 400 ml of ether, the solution is washed with water until neutral, dried and evaporated. The residue is crystallized from acetone. 2.23 g (73.6%) of the aimed compound are obtained; m.p.: 154°–157° C.

Analysis: calculated for $C_{27}H_{26}F_3NO_3$: C: 69.07%, H: 5.58%, F: 12.14%, N: 2.98%; found: C: 69.37%, H: 5.82%, F: 12.04%, N: 2.87%.

2-Phenyl-3,3,3-trifluoro-1-(4-methoxymethoxy-phenyl)-1-[4-(2-morpholinoethoxy)-phenyl]-propene, applied as starting substance, is prepared as follows:

9.6 g (120 mmoles) of chloromethyl ether and 8.4 g (210 mmoles) of powdered sodium hydroxide are added to a solution of 27.7 g (76 mmoles) of 2-phenyl-3,3,3-trifluoro-1-(4-fluorophenyl)-1-(4-hydroxyphenyl)-propane in 100 ml of benzene, prepared as described in Example 22, and the mixture is boiled for one hour. The reaction mixture is diluted with 150 ml of benzene, washed with a 20% aqueous ammonium chloride solution until neutral, dried and evaporated. The residue is dissolved in benzene and passed through a chromatographic column filled with 650 g of silica gel. The first eluate fractions are combined and evaporated to obtain 20.66 g (66.6%) of 2-phenyl-3,3,3-trifluoro-1-(4-fluorophenyl)-1-(4-methoxymethoxy-phenyl)-propane, which is applied in the subsequent step without purification.

22.7 g (100 mmoles) of 2,3-dichloro-5,6-dicyano-1,4-benzoquinone are added to a solution of 19.70 g (48.7 mmoles) of the above product in 100 ml of dry benzene. The mixture is boiled for 17 hours and then processed as described in Example 7. The product is crystallized from isopropanol. 7.20 g (36.7%) of 2-phenyl-3,3,3-trifluoro-1-(4-fluorophenyl)-1-(4-methoxy-methoxy-phenyl)-propene are obtained; m.p.: 66°–68° C.

Analysis: calculated for $C_{28}H_{18}F_4O_2$: C: 68.65%, H: 4.51%, F: 18.89%; found: C: 68.50%, H: 4.73%, F: 19.01%.

0.28 g (0.012 g.-atoms) of sodium are dissolved in 4.72 g (36 mmoles) of (2-hydroxyethyl)-morpholine, 2.40 g (6 mmoles) of the above product are added, and the mixture is heated at 150° C. for one hour. The mixture is cooled, diluted with 100 ml of ether, washed with water until neutral and dried. 3.08 g (100%) of 2-phenyl-3,3,3-trifluoro-1-(4-methoxymethoxy-phenyl)-1-[4-(2-morpholinoethoxy)-phenyl]-propene are obtained as a resinous substance. This product is utilized in the subsequent step without purification.

EXAMPLE 34

Preparation of
2-phenyl-3,3,3-trifluoro-1-(4-hydroxyphenyl)-1-[4-(2-methylamino-ethoxy)-phenyl]-propene hydrochloride 1.5 ml of a 9% methanolic hydrochloric acid are added to a solution of 1.50 g (3.28 mmoles) of 2-phenyl-3,3,3-trifluoro-1-[4-(2-methylaminoethoxy)-phenyl]-1-(4-methoxymethoxy-phenyl)-propene in 15 ml of methanol, and the mixture is boiled for one hour. The solution is evaporated to dryness, and the residue is crystallized from isopropanol. 1.06 g (71.6%) of the aimed compound are obtained; m.p.: 213°–218° C.

Analysis: calculated for $C_{24}H_{23}ClF_3NO_2$: C: 64.07%, H: 5.15%, Cl: 7.88%, F: 12.67%, N: 3.11%; found: C: 64.74%, H: 5.53%, Cl: 8.01%, F: 12.45%, N: 3.03%.

2-Phenyl-3,3,3-trifluoro-[4-(2-methylaminoethoxy)-phenyl]-1-(4-methoxymethoxy-phenyl)-propene, applied as starting substance, is prepared as follows:

0.28 g (0.012 g.-atoms) of sodium are dissolved in 2.70 g (36 mmoles) of N-methylamino-ethanol, 2.36 g (5.86 mmoles) of 2-phenyl-3,3,3-trifluoro-1-(4-fluorophenyl)-1-(4-methoxymethoxy-phenyl)-propene, prepared as described in Example 33, are added, and the mixture is heated at 150° C. for one hour. The mixture is cooled, diluted with 100 ml of ether, washed with water until neutral, dried and evaporated. The residue is crystallized from hexane. 1.94 g (72.4%) of 2-phenyl-3,3,3-trifluoro-1-[4-(2-methylaminoethoxy)-phenyl]-1-(4-methoxymethoxy-phenyl)-propene are obtained; m.p.: 87°–90° C.

Analysis: calculated for $C_{26}H_{26}F_3NO_3$: C: 69.25%, H: 5.73%, F: 12.46%, N: 3.06%; found: C: 70.08%, H: 5.65%, F: 12.66%, N: 3.16%.

EXAMPLE 35

Preparation of
(E)-1,2-diphenyl-3,3,3-trifluoro-1-[4-(2-heptamethyleneimino-ethoxy)-phenyl]-propene 2.32 g (20 mmoles) of heptamethyleneimine are added to a solution of 4.47 g (10 mmoles) of (E)-1-[4-(2-bromoethoxy)-phenyl]-1,2-diphenyl-3,3,3-trifluoro-propene, prepared as described in Example 7, in 30 ml of ethanol, and the mixture is boiled for 5 hours. The reaction mixture is evaporated to dryness. Thereafter one proceeds as described in Example 1, and crystallizes the product from hexane. 3.22 g (67%) of the desired compound are obtained; m.p.: 73°–77° C.

Analysis: calculated for $C_{30}H_{32}F_3NO$: C: 75.13%, H: 6.73%, F: 11.88%, N: 2.92%; found: C: 75.11%, H: 6.75%, F: 11.88%, N: 2.98%.

EXAMPLE 36

Preparation of
(E)-1-[4-(2-diethylaminoethoxy)-phenyl]-1,2-diphenyl-3,3,3-trifluoro-propene picrate 5.37 g (12 mmoles) of (E)-1-[4-(2-bromoethoxy)-phenyl]-1,2-diphenyl-3,3,3-trifluoro-propene, prepared as described in Example 7, are boiled with 8.8 g of diethylamino for 5 hours. The reaction mixture is diluted with 50 ml of benzene, washed with water until neutral, dried and evaporated. The residue is dissolved in 20 ml of 95% ethanol, and a solution of 3.22 g (14 mmoles) of picric acid in 32 ml of 95% ethanol is added. The separated crystals are filtered off, washed with ethanol and ether. 6.46 g (80.4%) of the aimed compound are obtained; m.p.: 131°–135° C.

Analysis: calculated for $C_{33}H_{31}F_3N_4O_8$: C: 59.28%, H: 4.67%, F: 8.52%, N: 8.40%; found: C, 59.55%, H: 4.78%, F: 8.73%, N: 8.35%.

EXAMPLE 37

Preparation of
(E)-1-[4-(2-dimethylaminoethoxy)-phenyl]-1,2-diphenyl-3,3,3-trifluoro-propene sulfate 0.03 ml (0.55 mmoles) of 98% sulfuric acid are added to a solution of 0.205 g (0.5 mmoles) of (E)-1-[4-(2-dimethylaminoethoxy)-phenyl]-1,2-diphenyl-3,3,3-trifluoro-propene in 1.5 ml of isopropanol. The separated crystals are filtered off, washed with ether, and the crude product is recrystallized from isopropanol. 0.22 g (84.6%) of the aimed compound are obtained; m.p.: 150°–153° C.

Analysis: calculated for $C_{25}H_{26}F_3NO_5S$: C: 59.93%, H: 5.14%, F: 11.19%, N: 2.75%, S: 6.29%; found: C: 59.07%, H: 5.30%, F: 11.29%, N: 2.70%, S: 6.46%.

(E)-1-[4-(2-Dimethylaminoethoxy)-phenyl]-1,2-diphenyl-3,3,3-trifluoro-propene, applied as starting substance, is prepared as follows:

10 ml of a 40% aqueous solution of dimethylamine are added to a solution of 5.37 g (12 mmoles) of (E)-1-[4-(2-bromoethoxy)-phenyl]-1,2-diphenyl-3,3,3-trifluoro-propene, prepared as described in Example 7, in 10 ml of ethanol. The mixture is allowed to stand for 3–4 days, then evaporated, the residue is diluted with 50 ml of benzene, the resulting solution is washed with water until neutral, dried and evaporated. The residue is crystallized from hexane. 4.26 g (86.2%) of (E)-1-[4-(2-dimethylaminoethoxy)-phenyl]-1,2-diphenyl-3,3,3-trifluoro-propene are obtained; m.p.: 90°–91° C.

Analysis: calculated for $C_{25}H_{24}F_3NO$: C: 72.98%, H: 5.88%, F: 13.85%, N: 3.40%; found: C: 72.80%, H: 5.51%, F: 14.01%, N: 3.53%.

EXAMPLE 38

Preparation of
(E)-1,2-diphenyl-3,3,3-trifluoro-1-[4-(2-/4-(2-hydroxyethyl)-piperazino/-ethoxy)-phenyl]-propene mesylate A solution of 0.2 g (2 mmoles) of methanesulfonic acid in 2 ml of isopropanol is added to a solution of 0.50 g (1 mmole) of (E)-1,2-diphenyl-3,3,3-trifluoro-1-[4-(2-/4-(2-hydroxyethyl)-piperazino/-ethoxy)-phenyl]-propene, prepared as described in Example 11, in 1 ml of isopropanol. The separated crystals are filtered off and washed with ether. 0.58 g (96.7%) of the aimed compound are obtained; m.p.: 203°–209° 1 C.

Analysis: calculated for $C_{31}H_{39}F_3N_2O_8S_2$: C: 54.06%, H: 5.71%, F: 8.28%, N: 4.07%, S: 9.31%; found: C: 53.71%, H: 5.90%, F: 8.42%, N: 3.81%, S: 9.03%.

EXAMPLE 39

Preparation of
(E)-1-[4-(2-aminoethoxy)-phenyl]-1,2-diphenyl-3,3,3-trifluoro-propene tosylate A solution of 0.20 g (1 mmole) of p-toluenesulfonic acid in 1 ml of isopropanol is added to a solution of 0.30 g (0.8 mmoles) of (E)-1-[4-(2-aminoethoxy)-phenyl]-1,2-diphenyl-3,3,3-trifluoro-propene, prepared as described in Example 8, in 0.5 ml of isopropanol. The separated crystals are filtered off and washed with ether. 0.37 g (84%) of the aimed compound are obtained; m.p.: 162°–163° C.

Analysis: calculated for $C_{30}H_{28}F_3NO_4S$: C: 64.85%, H: 5.08%, F: 10.26%, N: 2.52%, S: 5.77%; found: C: 64.98%, H: 5.03%, F: 10.53%, N: 2.23%, S: 5.93%.

EXAMPLE 40

Preparation of
(E)-1,2-diphenyl-3,3,3-trifluoro-1-[4-(2-/2-hydroxyethylamino/-ethoxy)-phenyl]-propene citrate A solution of 0.13 g (0.6 mmoles) of citric acid hydrate in 0.8 ml of acetone is added to a solution of 0.21 g (0.5 mmoles) of (E)-1,2-diphenyl-3,3,3-trifluoro-1-[4-(2-/2-hydroxyethylamino/-ethoxy)-phenyl]-propene, prepared as described in Example 12, in 0.2 ml of acetone. The mixture is cooled, the separated crystals are filtered off and washed with acetone. 0.18 g (58%) of the aimed compound is obtained; m.p.: 127°–129° C.

Analysis: calculated for $C_{31}H_{32}F_3NO_9$: C: 60.09%, H: 5.21%, F: 9.20%, N: 2.26%; found: C: 60.18%, H: 5.13%, F: 9.24%, N: 2.37%.

EXAMPLE 41

Preparation of
(E)-1,2-diphenyl-3,3,3-trifluoro-1-[4-(2-hexylaminoethoxy)-phenyl]-propene tosylate 2.23 g (5 mmoles) of (E)-1-[4-(2-bromoethoxy)-phenyl]-1,2-diphenyl-3,3,3-trifluoro-propene, prepared as described in Example 7, are dissolved in a mixture of 5.0 g (50 mmoles) of n-hexylamine and 10 ml of 2-methoxyethanol. The mixture is boiled for 30 minutes, then evaporated, and the residue is passed through a chromatographic column filled with 50 g of silica gel. The column is eluted with benzene. The fractions which are chromatographically uniform are combined and evaporated, the residue is dissolved in 5 ml of isopropanol, and a solution of 1.20 g (6 mmoles) of p-toluenesulfonic acid in 6 ml of isopropanol is added. The separated crystals are filtered off and washed with ether. 2.14 g (91.8%) of the aimed compound are obtained; m.p.: 151°–153° C.

Analysis: calculated for $C_{36}H_{40}F_3NO_4S$: C: 67.58%, H: 6.30%, F: 8.91%, N: 2.19%, S: 5.01%; found: C: 67.61%, H: 6.55%, F: 9.08%, N: 2.39%, S: 5.15%.

EXAMPLE 42

Preparation of
(E)-1,2-diphenyl-3,3,3-trifluoro-1-[4-(2-/3-hydroxy-propylamino/-ethoxy)-phenyl]-propene 2.23 g (5 mmoles) of (E)-1-[4-(2-bromoethoxy)-phenyl]-1,2-diphenyl-3,3,3-trifluoro-propene, prepared as described in Example 7, are dissolved in a mixture of 3.80 g of 1-amino-3-propanol and 10 ml of 2-methoxyethanol. The mixture is boiled for 30 minutes and then processed as described in Example 2. The mixture is crystallized from a 1:1 mixture of ethyl acetate and hexane. 1.77 g (80.5%) of the aimed compound are obtained; m.p.: 97°–99° C.

Analysis: calculated for $C_{26}H_{26}F_3NO_2$: C: 70.73%, H: 5.94%, F: 12.91%, N: 3.17%; found: C: 70.71%, H: 5.94%, F: 12.83%, N: 3.23%.

EXAMPLE 43

Preparation of
(E)-1,2-diphenyl-3,3,3-trifluoro-1-[4-(2-nitroguanidino-ethoxy)-phenyl]-propene A solution of 3.83 g (10 mmoles) of (E)-1-[4-(2-aminoethoxy)-phenyl]-1,2-diphenyl-3,3,3-trifluoro-propene, prepared as described in Example 8, and 1.22 g (9 mmoles) of 2-methyl-1-nitro-2-isothiourea (L. Fishbein et al.: J. Am. Chem. Soc. 76, 1877 (1954) in 25 ml of ethanol is boiled for one hour. The reaction mixture is evaporated and the residue is crystallized from methanol. 2.78 g (66%) of the aimed compound are obtained; m.p.: 112°–116° C. (decomposition).

Analysis: calculated for $C_{24}H_{21}F_3N_4O_3$: C: 61.27%, H: 4.50%, F: 12.12%, N: 11.91%; found: C: 61.21;1 %, H: 4.80%, F: 12.27%, N: 11.62%.

EXAMPLE 44

Preparation of
(Z)-1,2-diphenyl-3,3,3-trifluoro-1-[4-(2-/2-hydroxyethylamino/-ethoxy)-phenyl]-propene fumarate 0.59 g (1.17 mmoles) of (Z)-1-[4-(2-bromoethoxy)-phenyl]-1,2-diphenyl-3,3,3-trifluoro-propene, prepared as described in Example 7, are dissolved in a mixture of 1.34 g of 2-aminoethanol and 1.5 ml of 2-methoxyethanol. The solution is boiled for 30 minutes and then processed as described in Example 2. The crude product is crystallized from a 1:3 mixture of ethyl acetate and hexane. 0.35 g (70%) of the base form of the title compound are obtained; m.p.: 81°–83° C. The free base is dissolved in 1.5 ml of ethanol, and an ethanol solution of 0.12 g (1 mmole) of fumaric acid is added. The separated crystals are filtered off and washed with ether. 0.28 g (62.2%) of the desired compound are obtained; m.p.: 168°–172° C.

Analysis: calculated for $C_{29}H_{28}F_3NO_6$: C: 64.08%, H: 5.19%, F: 10.49%, N: 2.58%; found: C: 64.40%, H: 5.32%, F: 10.65%, N: 2.85%.

EXAMPLE 45

Preparation of
threo-1,2-diphenyl-3,3,3-trifluoro-1-(4-propoxyphenyl)-propane 0.80 g (20 mmoles) of powdered sodium hydroxide and 6.8 g (40 mmoles) of n-propyl iodide are added to a solution of 3.42 g (10 mmoles) of threo-1,2-diphenyl-3,3,3-trifluoro-1-(4-hydroxyphenyl)-propane, prepared as described in Example 1, in 35 ml of dry benzene, and the mixture is boiled for 4 hours. The mixture is diluted with 50 ml of benzene, washed with water until neutral, dried and evaporated. The residue is crystallized from isopropanol. 3.32 g (85.5%) of the aimed compound are obtained; m.p.: 77°–80° C.

Analysis: calculated for $C_{24}H_{23}F_3O$: C: 74.98%, H: 6.03%, F: 14.83%; found: C: 75.01%, H: 6.20%, F: 14.95%.

EXAMPLE 46

Preparation of
threo-1-[4(/(3,4-epoxy)-2-hydroxy/-butoxy)-phenyl]-1,2-diphenyl-3,3,3-trifluoro-propane A mixture of 3.42 g (10 mmoles) of threo-1,2-diphenyl-3,3,3-trifluoro-1-(4-hydroxyphenyl)-propane, prepared as described in Example 1, and 17 ml of DL-diepoxybutane is heated at 100° C. for 0.5 hours. The reaction mixture is evaporated, the residue is diluted with 300 ml of ether, washed with water, dried and evaporated. The residue is crystallized from isopropanol. The obtained substance, weighing 3.22 g (75.2%; m.p.: 121°–126° C.), is subjected to chromatography in a 3:2 mixture of hexane and acetone, and the chromatographically uniform product is crystallized from isopropanol. 1.90 g (44.4%) of the desired compound are obtained; m.p.: 130°–133° C.

Analysis: calculated for $C_{25}H_{23}F_3O_3$: C: 70.08%, H: 5.41%, F: 13.30%; found: C: 70.30%, H: 5.74%, F: 13.09%.

What we claim is:

1. (E)-1,2-diphenyl-3,3,3-trifluoro-1-[4-(2-/2-hydroxyethylamino/-ethoxy)-phenyl]-propene.

* * * * *